(12) United States Patent
Young et al.

(10) Patent No.: US 11,851,643 B2
(45) Date of Patent: Dec. 26, 2023

(54) SELECTIVE THIN-FILM CULTURE DEVICE FOR ENUMERATING MICROORGANISMS

(71) Applicant: 3M INNOVATIVE PROPERTIES COMPANY, St. Paul, MN (US)

(72) Inventors: Alexi J. Young, St. Paul, MN (US);
Evan D. Brutinel, St. Paul, MN (US);
Patrick A. Mach, St. Paul, MN (US);
Adam J. Stanenas, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 693 days.

(21) Appl. No.: 16/977,244

(22) PCT Filed: May 2, 2019

(86) PCT No.: PCT/US2019/030297
§ 371 (c)(1),
(2) Date: Sep. 1, 2020

(87) PCT Pub. No.: WO2019/213332
PCT Pub. Date: Nov. 7, 2019

(65) Prior Publication Data
US 2021/0040434 A1 Feb. 11, 2021

Related U.S. Application Data

(60) Provisional application No. 62/666,346, filed on May 3, 2018.

(51) Int. Cl.
*C12M 1/34* (2006.01)
*C12M 1/00* (2006.01)
*C12M 1/12* (2006.01)
*C12Q 1/04* (2006.01)

(52) U.S. Cl.
CPC ............ *C12M 41/46* (2013.01); *C12M 23/14* (2013.01); *C12M 23/20* (2013.01); *C12M 25/02* (2013.01); *C12M 41/14* (2013.01); *C12Q 1/04* (2013.01)

(58) Field of Classification Search
CPC ................................................ A61K 49/0008
See application file for complete search history.

(56) References Cited

U.S. PATENT DOCUMENTS

| | | | |
|---|---|---|---|
| 3,929,583 A | 12/1975 | Sharpe | |
| 4,485,171 A | 11/1984 | Ikeda | |
| 4,565,783 A | 1/1986 | Hansen | |
| 5,089,413 A | 2/1992 | Nelson | |
| 5,232,838 A | 8/1993 | Nelson | |
| 5,364,766 A | 11/1994 | Mach | |
| 5,409,838 A | 4/1995 | Wickert | |
| 5,443,963 A | 8/1995 | Lund | |
| 5,462,860 A | 10/1995 | Mach | |
| 5,601,998 A | 2/1997 | Mach | |
| 5,635,367 A | 6/1997 | Lund | |
| 5,681,712 A | 10/1997 | Nelson | |
| 5,770,086 A | 6/1998 | Indriksons | |
| 6,063,590 A | 5/2000 | Brenner | |
| 7,371,464 B2 | 5/2008 | Sherman | |
| 7,695,818 B2 | 4/2010 | Sherman | |
| 2013/0344488 A1 | 12/2013 | Mach | |
| 2015/0252314 A1 | 9/2015 | Onji | |

FOREIGN PATENT DOCUMENTS

| | | |
|---|---|---|
| CA | 2176895 | 11/1996 |
| JP | H 05-13200 A | 2/1993 |
| JP | H07-75545 | 3/1995 |
| JP | H08-266268 | 10/1996 |
| JP | 2007124985 | 5/2007 |
| WO | WO 2001-59060 | 8/2001 |
| WO | WO 2005-058453 | 6/2005 |
| WO | WO 2014-054494 | 4/2014 |
| WO | WO 2017-019345 | 2/2017 |
| WO | WO 2018-061719 | 4/2018 |
| WO | WO 2018-125805 | 7/2018 |
| WO | WO 2018-187197 | 10/2018 |

OTHER PUBLICATIONS

International Search Report for PCT International Application No. PCT/US2019/030297, dated Aug. 7, 2019, 4 pages.

*Primary Examiner* — Brian Gangle
*Assistant Examiner* — Lakia J Jackson-Tongue
(74) *Attorney, Agent, or Firm* — Adrian L. Pishko

(57) ABSTRACT

A selective microbial detection device and methods of use are provided. The device includes a water-proof pouch that includes a first wall portion, a second wall portion, and a porous membrane filter disposed in the pouch between the first and second wall portions. The filter membrane divides the pouch into first and second compartments. The microbial detection device also includes an effective amount of a dry nutrient disposed in the first compartment, which contains sodium lauryl sulfate in an amount of 1.75 milligrams or greater per twelve square inches of the first wall portion. A dry, cold water-soluble gelling agent is adhered to the pouch in the first compartment and an absorbent pad is disposed in the second compartment. A sealable sample port provides access to deposit a liquid into the first compartment.

17 Claims, 5 Drawing Sheets

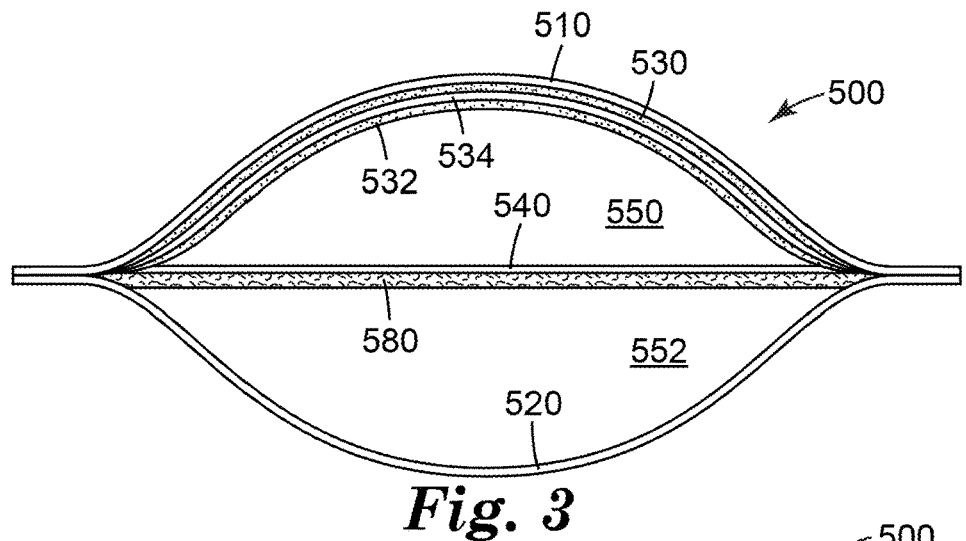
*Fig. 3*
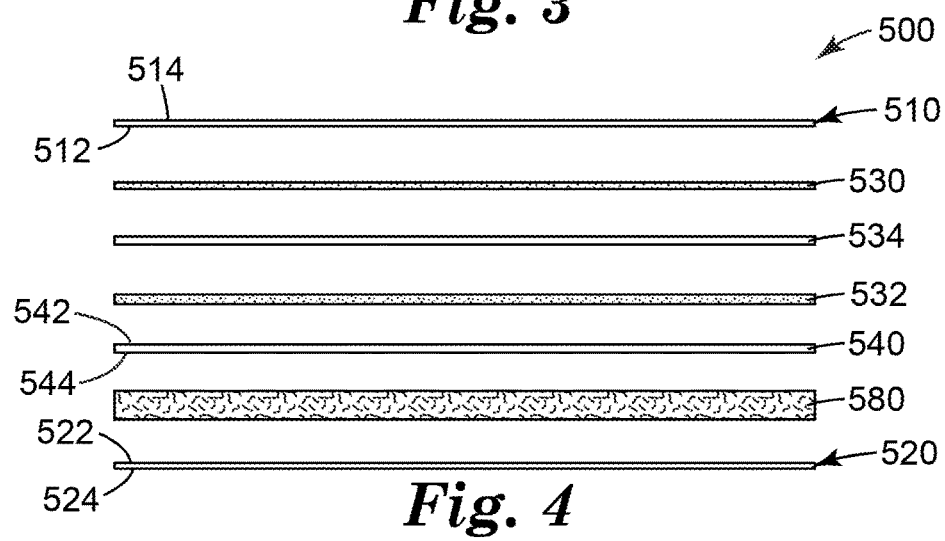
*Fig. 4*
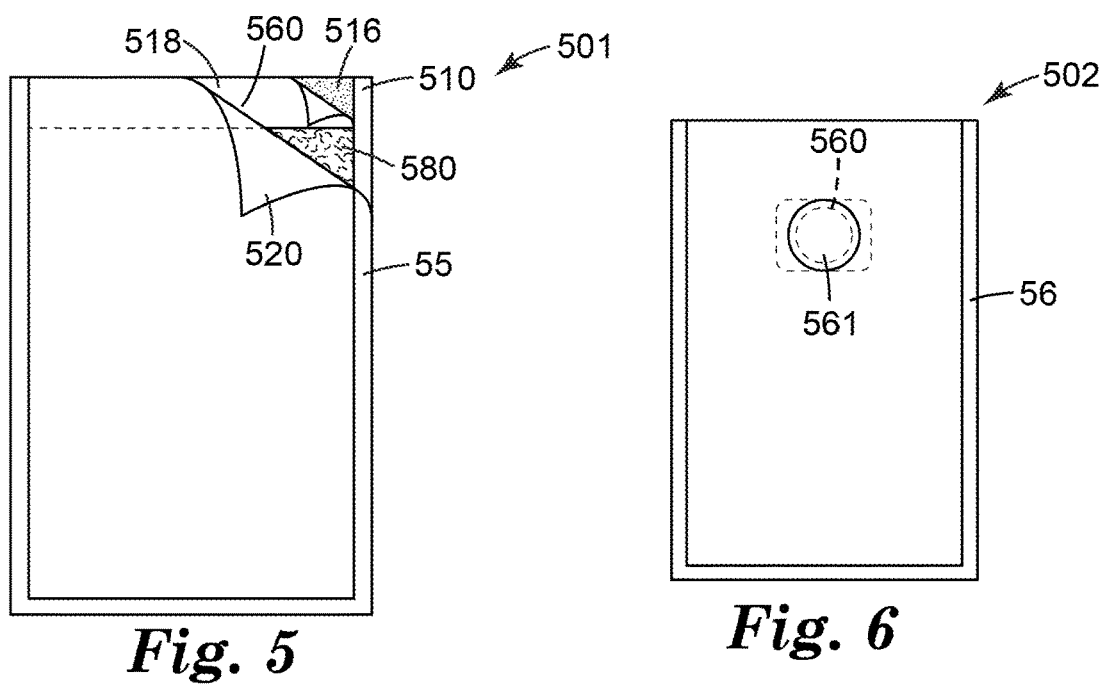
*Fig. 5*
*Fig. 6*

SELECTIVE THIN-FILM CULTURE DEVICE FOR ENUMERATING MICROORGANISMS

CROSS REFERENCE TO RELATED APPLICATIONS

This application is a national stage filing under 35 U.S.C. 371 of PCT/US2019/030297, filed May 2, 2019, which claims the benefit of U.S. Application No. 62/666,346, filed May 3, 2018, the disclosures of which are incorporated by reference in their entirety herein.

BACKGROUND

Many industries need to detect and quantify biological material in a sample, for instance, the determination of microbial concentration in food and water is an essential part of food and water quality testing. Similar demands arise from a multitude of industries including food, biotechnological, pharmaceutical, water treating industry, and also in medical microbiological diagnostics, environmental and scientific research. Samples are commonly scrutinized to, for instance, monitor microbial population in a production environment, in-process controls, post storage and also final product testing.

Classical methods for the examination of samples particularly liquid samples typically demands incubation time or reaction time for analysis. Analysis may involve several different kinds of chemical, biochemical, physical or optical techniques and require many hours or even days for incubation and subsequent analysis. Reducing the time and/or labor for quantitative and qualitative analysis of samples is essential for making rapid decisions in quality and process control operations.

With regard to testing of aqueous biological samples, it is advantageous to test large-volume samples, in order to detect relatively low concentrations of certain microorganisms (e.g., pathogenic microorganisms). Large-volume samples are often concentrated by filtration or centrifugation, for example, in order to make the sample more amenable to the traditional detection techniques (e.g., culture detection, molecular genetic detection, and immunological detection).

In food and beverage safety testing, the presence or absence of coliform bacteria is considered to be important evidence of quality. The amount of coliform bacteria permitted in beverages and in certain foods (for example, dairy products) is regulated in many countries around the world. Coliform bacteria include fecal coliforms, such as *Escherichia coli*. The presence of fecal coliforms in a food or water sample is used as a primary indicator of fecal contamination of the food or water and of the possible presence of other pathogenic microorganisms.

There is a need for easier methods for selectively enumerating viable coliform and *E. coli* microorganisms in food and beverage samples, including relatively large volumes of samples.

SUMMARY

The present disclosure generally relates to a device for selectively culturing and detecting microorganisms. In addition, the present disclosure relates to a method for culturing and detecting microorganisms in a sample. In particular, the present disclosure relates to culturing and detecting microorganisms present in a relatively large sample volume in a self-contained thin-film culture device. The present disclosure provides devices and methods for detecting and/or enumerating target microorganisms in relatively-large (e.g., about 25 mL to about 150 mL) liquid samples. It is now known that a self-contained device can include all of the components needed to concentrate microorganisms from a large liquid sample, immobilize the microorganisms in a cold water-soluble gelling agent, and provide a moist nutrient environment sufficient to grow and detect colonies of the microorganisms. Advantageously, in at least certain embodiments, the device can be used to selectively detect and/or enumerate coliforms such as *E. coli*) present in a liquid sample.

In a first aspect, a microbial detection device is provided. The microbial detection device includes a water-proof pouch, a dry cold water-soluble gelling agent adhered to the pouch, and an absorbent pad. The water-proof pouch includes a first wall portion having an inner surface and an outer surface and a second wall portion having an inner surface and an outer surface. The water-proof pouch also includes a porous membrane filter disposed in the pouch between the inner surface of the first wall portion and the inner surface of the second wall portion, the membrane filter having a first major surface and a second major surface opposite the first major surface. The water-proof pouch further includes a first compartment defined in part by inner surface of the first wall portion and defined in part by the first major surface of the membrane filter, and a sealable sample port that provides access to deposit a liquid into the first compartment. Additionally, the water-proof pouch contains an effective amount of a dry nutrient disposed in the first compartment, the dry nutrient comprising sodium lauryl sulfate in an amount of 1.75 milligrams (mg) or greater per 12 square inches ($in^2$) of the inner surface of the first wall portion. The water-proof pouch also includes a second compartment defined in part by the inner surface of the second wall portion and defined in part by the second major surface of the membrane filter. The membrane filter permits passage of aqueous liquids from the first compartment to the second compartment and prevents passage of particles of a predetermined size from the first compartment to the second compartment. The dry cold water-soluble gelling agent is adhered to the pouch in the first compartment, and the absorbent pad is disposed in the second compartment.

In a second aspect, a method is provided. The method includes placing a predetermined volume of aqueous sample into the first compartment of the microbial detection device of the first aspect; sealing the sample port; incubating the device for a period of time at a temperature that facilitates growth and detection of a target microorganism; and detecting a presence or an absence of a colony of the target microorganism in the device.

The features and advantages of the present invention will be understood upon consideration of the detailed description of the preferred embodiment as well as the appended claims. These and other features and advantages of the invention may be described below in connection with various illustrative embodiments of the invention.

The above summary of the present invention is not intended to describe each disclosed embodiment or every implementation of the present invention. The figures and the detailed description which follow more particularly exemplify illustrative embodiments. Other features, objects and advantages will become apparent from the description and drawings, and from the claims.

BRIEF DESCRIPTION OF DRAWINGS

FIG. 3 is a cross-sectional view, taken along the line 3-3, of the device of FIG. 2.

FIG. 4 is an exploded cross-sectional view, of the device of FIG. 2.

FIG. 5 is a plan view, partially in section, of an alternative embodiment of the device of FIG. 1, showing an adhesive strip and a release liner releasably adhered thereto that form a sealable sample port.

FIG. 6 is a plan view of an alternative embodiment of a device according to the present disclosure, wherein the device comprises a sealable sample port with a screwcap.

Figure 1:
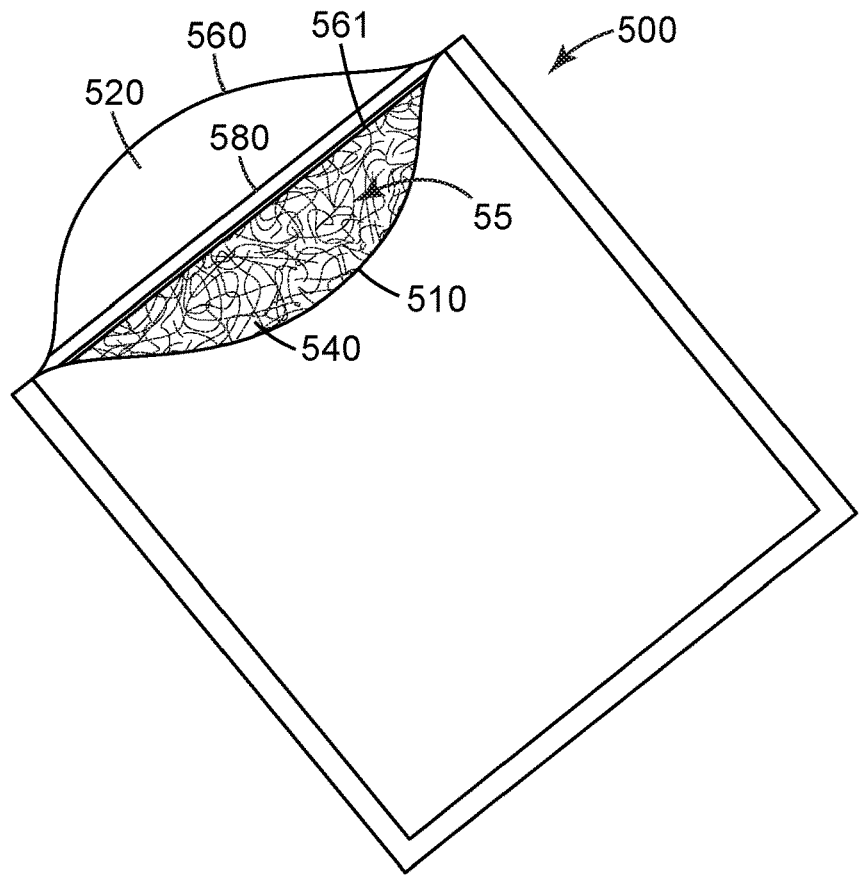
FIG. 1 is a perspective view of one embodiment of a device according to the present disclosure.

While the above-identified figures set forth several embodiments of the disclosure other embodiments are also contemplated, as noted in the description. The figures are not necessarily drawn to scale. In all cases, this disclosure presents the invention by way of representation and not limitation. It should be understood that numerous other modifications and embodiments can be devised by those skilled in the art, which fall within the scope and spirit of the principles of the invention.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways.

Glossary:

Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

"Gram positive bacteria" collectively refers to a group of bacteria that give a positive result in the Gram stain test. These bacteria have a cell wall composed of a thick layer of a substance called peptidologlycan.

"Gram negative bacteria" collectively refers to a group of bacteria that give a negative result in the Gram stain test. These bacteria have a cell wall composed of a thin layer of a substance called peptidologlycan.

"Coliform bacteria" collectively refers to a group of several genera (e.g., *Citrobacter, Enterobacter, Hafnia, Klebsiella, Serratia* and *Escherichia*) of bacteria that have the ability to ferment lactose with a resultant production of acid and gas. Most coliform bacteria are generally considered nonpathogenic to humans. However, some coliform bacteria (e.g., *Escherichia coli (E. coli.)*) include strains that are highly pathogenic. Coliforms are found in the fecal matter of mammals and are commonly used as an indicator of fecal contamination of food and/or water.

The terms "culture" and "growth" of microorganisms as used herein refers to the method of multiplying microbial organisms by letting them reproduce in predetermined culture media under conditions conducive for their growth. More particularly it is the method of providing a suitable culture medium and conditions to facilitate at least one cell division of a microorganism. Culture media are solid, semi-solid or liquid media containing all of the nutrients and necessary physical growth parameters necessary for microbial growth.

"Enrichment" refers to the culture method of selectively enriching the growth of a specific microorganism by providing medium and conditions with specific and known attributes that favors the growth of that particular microorganism. The enrichment culture's environment will positively influence the growth of a selected microorganism and/or negatively influence the growth of other microorganisms.

"Cold-water-soluble" refers to material which forms a solution in water at room temperature (i.e., about 25° C.).

"Hydrophobic" refers to a material that exhibits a water contact angle of 90° or larger on its surface.

"Opaque" refers to a substrate having at most 10% visible light transmission.

"Powder" refers to a finely divided particulate material having an average diameter in a range from 0.1 micrometer up to 400 micrometers.

"Reconstituted medium" refers to a solution or gel formed from the reconstitution of a cold-water-soluble powder with an aqueous liquid.

"Substantially impermeable to microorganisms and water vapor", as used herein, refers to a cover sheet that prevents undesired contamination and hydration of underlying layers of cold-water-soluble powder during shipping, storage, and use of thin film culture device(s), and avoids desiccation of the reconstituted medium, such that the reconstituted medium is suitable to support the growth of microorganisms during an incubation period.

"Substantially water-free", as used herein, designates a water content no greater than about the water content of the ambient environment.

"Test sample", as used herein, refers to a component or portion taken from a food product, a human or animal test subject, pharmaceutical or cosmetic commodity, soil, water, air or other environmental source, or any other source from which a presence and, optionally, an enumeration of aerobic and/or aerotolerant bacteria is to be determined. A test sample may be taken from a source using techniques known to one skilled in the art including, for example, pouring, pipetting, swabbing, filtering, and contacting. In addition, the test sample may be subjected to various sample preparation processes known in the art including, for example, blending, stomaching, homogenization, enrichment, selective enrichment, or dilution.

"Transparent" refers to a substrate having at least 90% visible light transmission.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a culture device comprising "an" indicator agent can be interpreted to mean that the culture device can comprise "one or more" indicator agents.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties). The term "substantially", unless otherwise specifically defined, means to a high degree of approximation (e.g., within +/−10% for quantifiable properties) but again without requiring absolute precision or a perfect match. Terms such as same, equal, uniform, constant, strictly, and the like, are understood to be within the usual tolerances or measuring error applicable to the particular circumstance rather than requiring absolute precision or a perfect match.

The present disclosure provides devices and methods for detecting and/or enumerating target microorganisms in relatively-large (e.g., about 25 mL to about 150 mL) liquid samples. It is now known that a self-contained device can include all of the components needed to concentrate microorganisms from a liquid sample, immobilize the microorganisms in a matrix, and provide a moist nutrient environment sufficient to grow and detect colonies of the microorganisms. Advantageously, the device can be used to detect and/or enumerate microorganisms present in a liquid sample, and in some instances selectively between Gram negative and Gram positive bacteria. In addition, the self-contained device provides certain advantages of thin-film culture devices such as, for example, sample-ready (i.e., just add liquid sample and then incubate), ease of use, portability, compactness, and a relatively long shelf-life.

A device of the present disclosure can be used to enumerate microorganisms in a sample of water (e.g., surface water, process water, potable water). The water can be interrogated for the presence of certain target microorganisms including, for example, coliforms, fecal coliforms, $E.\ coli$, and/or total aerobic count or aerobic plate count (APC). The presence of fecal coliforms in a water sample can indicate contamination of the water with human fecal material, which may contain certain pathogenic bacteria and/or viruses. The present disclosure provides culture devices that can be used to grow colony-forming units (CFUs) of coliform bacteria in a semi-solid culture medium and to differentially enumerate coliform CFUs and $E.\ coli$ CFUs. Typically, such culture devices include a plurality of compounds that enhance beta-glucuronidase activity in $E.\ coli$ and can be particularly useful for detecting and differentiating colonies of beta-glucuronidase-positive $E.\ coli$ I, for example constitutive and inducible beta-glucuronidase-positive $E.\ coli$, thereby providing more-accurate counts of the microorganisms present in a sample.

In a first aspect, a microbial detection device is provided. The microbial detection device includes a water-proof pouch, a dry cold water-soluble gelling agent adhered to the pouch, and an absorbent pad. The water-proof pouch includes a first wall portion having an inner surface and an outer surface and a second wall portion having an inner surface and an outer surface. The water-proof pouch also includes a porous membrane filter disposed in the pouch between the inner surface of the first wall portion and the inner surface of the second wall portion, the membrane filter having a first major surface and a second major surface opposite the first major surface. The water-proof pouch further includes a first compartment defined in part by inner surface of the first wall portion and defined in part by the first major surface of the membrane filter, and a sealable sample port that provides access to deposit a liquid into the first compartment. Additionally, the water-proof pouch contains an effective amount of a dry nutrient disposed in the first compartment, the dry nutrient comprising sodium lauryl sulfate in an amount of 1.75 milligrams (mg) or greater per 12 square inches ($in^2$) of the inner surface of the first wall portion. The water-proof pouch also includes a second compartment defined in part by the inner surface of the second wall portion and defined in part by the second major surface of the membrane filter. The membrane filter permits passage of aqueous liquids from the first compartment to the second compartment and prevents passage of particles of a predetermined size from the first compartment to the second compartment. The dry cold water-soluble gelling agent is adhered to the pouch in the first compartment, and the absorbent pad is disposed in the second compartment.

For instance, a microbial detection device can comprise:
a water-proof pouch comprising:
  a first wall portion having an inner surface and an outer surface;
  a second wall portion having an inner surface and an outer surface;
  a porous membrane filter disposed in the pouch between the inner surface of the first wall portion and the inner surface of the second wall portion, the membrane filter having a first major surface and a second major surface opposite the first major surface;
  a first compartment defined in part by inner surface of the first wall portion and defined in part by the first major surface of the membrane filter;
  a sealable sample port that provides access to deposit a liquid into the first compartment;
  an effective amount of a dry nutrient disposed in the first compartment, the dry nutrient comprising sodium lauryl sulfate in an amount of 1.75 mg or greater per 12 $in^1$ of the inner surface of the first wall portion;
  a second compartment defined in part by the inner surface of the second wall portion and defined in part by the second major surface of the membrane filter;
  wherein the membrane filter permits passage of aqueous liquids from the first compartment to the second compartment and prevents passage of particles of a predetermined size from the first compartment to the second compartment;

a dry cold water-soluble gelling agent adhered to the pouch in the first compartment; and an absorbent pad disposed in the second compartment.

FIGS. 1-4 show various views of one embodiment of a device 500 according to at least one embodiment of the present disclosure. The device 500 comprises a waterproof pouch 55 defined by at least one wall. The at least one wall comprises a first wall portion 510 and a second wall portion 520. The first wall portion 510 has an inner surface 512 and an outer surface 514. The second wall portion 520 has an inner surface 522 and an outer surface 524. Disposed in the pouch 55 between the inner surface 512 of the first wall portion 510 and the inner surface 522 of the second wall portion 520 is a membrane filter 540. The membrane filter has a first major surface 542 and a second major surface 544 opposite the first major surface.

Although the first wall portion 510 and second wall portion 520 may be distinct portions of a unitary pouch or bag, in any embodiment, the first wall portion and second wall portion alternatively may consist of separate sheets of polymeric film that are joined together (e.g., heat-sealed and/or adhesively sealed along the edges) to form the pouch, as shown in FIG. 5, for example, and described herein.

The pouch 55 is divided into at least two compartments (first compartment 550 and second compartment 552, respectively). The first compartment 550 is defined in part by the inner surface 512 of the first wall portion 510 and also defined in part by the first major surface 542 of the membrane filter 540. The first compartment 550 has a sealable sample port 560. In the illustrated embodiment of FIGS. 1-3, the sealable sample port 560 is simply an opening 561 along a portion of the perimeter of the pouch 55. Nonlimiting exemplary means for closing the opening 561 are discussed herein. The second compartment 552 is defined in part by the inner surface 522 of the second wall portion 520 and defined in part by the second major surface 544 of the membrane filter 540.

The first compartment 550 is configured to receive a volume of liquid sample to be tested for presence of target microorganisms. The volume of liquid the first compartment 550 can receive will be influenced by several features of the device including, for example, the dimensions (e.g., the length "L" and width "W" shown in FIG. 2) of the first compartment and the flexibility of the materials (e.g., the first wall portion 510 and the membrane filter 540) that define the first compartment. The second compartment 552 is configured to receive a volume of liquid approximately equal to the volume of liquid sample to be tested. Thus, the pouch of a device of the present disclosure may be dimensioned to hold up to about twice the volume of the sample to be tested.

In any embodiment, a device of the present disclosure is configured to test (i.e., configured to receive) at least about 25 milliliters of liquid sample. In any embodiment, a device of the present disclosure is configured to test at least about 50 milliliters of liquid sample. In any embodiment, a device of the present disclosure is configured to test at least about 75 milliliters of liquid sample. In any embodiment, a device of the present disclosure is configured to test at least about 100 milliliters of liquid sample. In any embodiment, a device of the present disclosure is configured to test at least about 125 milliliters of liquid sample. In any embodiment, a device of the present disclosure is configured to test at least about 150 milliliters of liquid sample. Thus, in any embodiment, the device according to the present disclosure is configured to receive at least about 25 mL, at least about 50 mL, at least about 75 mL, at least about 100 mL, at least about 125 mL, at least about 150 mL of liquid sample (e.g., aqueous liquid sample). Accordingly, in any embodiment, the first compartment of the device is configured to receive at least about 25 mL, at least about 50 mL, at least about 75 mL, at least about 100 mL, at least about 125 mL, at least about 150 mL of liquid sample (e.g., aqueous liquid sample).

The pouch 55 further comprises a substantially dry microbial growth nutrient composition disposed on a portion of the pouch (e.g., the first wall portion 510 of the pouch) in the first compartment 550. In any embodiment, a device of the present disclosure comprises an effective amount of one or more dry nutrients (e.g., a nutrient medium selected to support growth of the target microorganism). In any embodiment, the one or more dry nutrients may be disposed in the device (e.g., in the first compartment) as a dry powder or agglomerated powder. In any embodiment, the one or more dry nutrients can be adhered to the pouch (e.g., adhered to an inner surface of the first wall portion in the first compartment). In any embodiment, the one or more dry nutrients may be adhered to an adhesive layer that is adhered to an inner surface the first wall portion.

The microbial growth nutrient composition typically comprises at least one nutrient selected from the group consisting of a meat peptone, a casein peptone, a gelatin peptone, a soy peptone, a beef extract, a yeast extract, lactose, glucose, dextrose, tryptose, galactose, tryptone, a fat, a mineral, or a vitamin. Further, non-limiting examples of nutrients, additional gelling agents, and mixtures thereof for supporting growth of microorganisms in a device of the present disclosure include those described in U.S. Pat. Nos. 4,565,783; 5,089,413; 5,232,838; 5,364,766; 5,443,963; 5,462,860; 5,601,998; 5,635,367; and 5,681,712.

Suitable coat weight of the dry nutrient is 50 milligrams (mg) per 24 square inches ($in^2$) or greater, 75 mg per 24 $in^2$ or greater, 100 mg per 24 $in^2$ or greater, 125 mg per 24 $in^2$ or greater, 150 mg per 24 $in^2$ or greater, 175 mg per 24 $in^2$ or greater, 200 mg per 24 $in^2$ or greater, 225 mg per 24 $in^2$ or greater, 250 mg per 24 $in^2$ or greater, 275 mg per 24 $in^2$ or greater, or 300 mg per 24 $in^2$ or greater; and 550 mg per 24 $in^2$ or less, 525 mg per 24 $in^2$ or less, 500 mg per 24 $in^2$ or less, 475 mg per 24 $in^2$ or less, 450 mg per 24 $in^2$ or less, 425 mg per 24 $in^2$ or less, 400 mg per 24 $in^2$ or less, 375 mg per 24 $in^2$ or less, or 350 mg per 24 $in^2$ or less. Stated another way, the coat weight of the substantially dry nutrient composition may range from 50 to 550 mg per 24 $in^2$, or from 250 to 500 mg per 24 $in^2$. In some embodiments, the dry nutrient composition comprises a microbial growth nutrient and at least one cold-water-soluble gelling agent.

The substantially dry microbial growth nutrient composition further comprises an effective amount of at least one agent, namely sodium lauryl sulfate, that selectively inhibits growth of certain microorganisms, such as Gram positive bacteria and non-coliform microorganisms. Sodium lauryl sulfate is also known as sodium dodecyl sulfate (SDS), which is commercially available from chemical suppliers such as Sigma Aldrich (St. Louis, MO) and TCI America (Portland, OR). The agent typically provides a competitive advantage, for instance, for growth of coliform microorganisms, relative to at least one non-coliform microorganism, in the device of the present disclosure. In certain embodiments, the effective amount of the agent is selected so that, when a predetermined volume of aqueous liquid is deposited in the growth zone, the rehydrated culture medium has a concentration of the agent is sufficiently high to selectively inhibit growth of non-coliform microorganisms but not so high that it substantially inhibits growth of coliform microorganisms (i.e., the coliform microorganisms form observable and identifiable colonies within about 24 hours of incubation at a temperature of about 37° C. to about 45° C.).

It was unexpectedly discovered that a significantly higher loading of sodium lauryl sulfate in the microbial detection device according to the present disclosure still allows bacteria to grow, as compared to the sodium lauryl sulfate loading in typical commercially available culture broths (e.g., available under the trade designation ACUMEDIA LAURYL SULFATE BROTH available from Neogen (Lansing, MI). For instance, while a typical thin-film culture device might contain approximately 0.175 mg of sodium lauryl sulfate per 12 square inches of a film surface, microbial detection devices according to the present disclosure contain 1.75 mg or greater of sodium lauryl sulfate per 12 $in^2$ of a surface in the device (e.g., the inner surface of the first wall portion of the water-proof pouch). It is generally known that the inclusion of a large amount of sodium lauryl sulfate will inhibit microorganism growth, thus it was unexpected that ten times the amount typically present in a commercially available culture broth was found not to inhibit the growth of bacteria.

In certain embodiments, the microbial detection device comprises 2 mg or greater of sodium lauryl sulfate per 12 $in^2$ (77.4 square centimeters ($cm^2$)) of a surface, 2.25 mg or greater, 2.5 mg or greater, 2.75 mg or greater, 3 mg or greater, 3.5 mg or greater, 3.6 mg or greater, 3.7 mg or greater, 3.8 mg or greater, 3.9 mg or greater, 4 mg or greater, 4.1 mg or greater, 4.2 mg or greater, 4.3 mg or greater, 4.4 mg or greater, 4.5 mg or greater, 4.6 mg or greater, 4.7 mg or greater, 4.8 mg or greater, 4.9 mg or greater, 5 mg or greater, 5.1 mg or greater, 5.2 mg or greater, 5.3 mg or greater, 5.4 mg or greater, 5.5 mg or greater, 5.6 mg or greater, 5.7 mg or greater, 5.8 mg or greater, 5.9 mg or greater, 6 mg or greater, 6.1 mg or greater, 6.2 mg or greater, 6.3 mg or greater, 6.4 mg or greater, 6.5 mg or greater, 6.6 mg or greater, 6.7 mg or greater, 6.8 mg or greater, 6.9 mg or greater, 7 mg or greater, 7.1 mg or greater, 7.2 mg or greater, 7.3 mg or greater, 7.4 mg or greater, 7.5 mg or greater, 7.6 mg or greater, 7.7 mg or greater, 7.8 mg or greater, 7.9 mg or greater, or 8 mg or greater, of sodium lauryl sulfate per 12 $in^2$ of a surface (e.g., the inner surface of the first wall portion of the water-proof pouch). In certain embodiments, the microbial detection device according to the present disclosure preferably contains 6.7 mg or greater, 6.8 mg or greater, 6.9 mg or greater, or 7 mg or greater of sodium lauryl sulfate per 12 $in^2$ of a surface. In some embodiments, the microbial detection device contains 16 mg or less of sodium lauryl sulfate per 12 $in^2$ of a surface. In certain embodiments, the microbial detection device according to the present disclosure contains an effective amount of sodium lauryl sulfate that inhibits growth of gram positive bacteria and/or non-coliform microorganisms while allowing gram negative bacteria such as coliform microorganisms to grow.

The pouch 55 additionally comprises an adhesive composition adhered to the microbial growth nutrient composition. Suitable adhesives are transparent when wetted with water. As noted above, the adhesive composition is often water insoluble. In certain embodiments, the adhesive composition comprises a solvent based adhesive. The adhesive often is a pressure sensitive adhesive. In any embodiment, each one or more layers of adhesive is water-insoluble and non-inhibitory to the growth of microorganisms, plus sufficiently transparent when wet to enable the detection and optionally enumeration of microorganism colonies through the adhesive. For instance, the adhesive may be a pressure-sensitive adhesive such as a water-insoluble adhesive comprising a copolymer of an alkyl acrylate monomer and an alkyl amide monomer. Preferably the weight ratio of alkyl acrylate monomer to alkyl amide monomer in these copolymers is from about 90:10 to 99:1, more preferably 94:6 to 98:2. The alkyl acrylate monomer comprises a lower alkyl (C2 to C10) monomer of acrylic acid, including, for example, isooctyl acrylate (IOA), 2-ethylhexyl acrylate, butyl acrylate, ethyl acrylate, isoamyl acrylate, and mixtures thereof, while the alkyl amide monomer can comprise, without limitation, acrylamide (ACM), methacrylamide, N-vinylpyrrolidone (NVP), N-vinylcaprolactam (NVCL), N-vinyl-2-piperidine, N-(mono- or di-lower alkyl (C2 to C5))(meth)acrylamides, N-methyl(meth)acrylamide, N,N-dimethyl(meth) acrylamides, or mixtures thereof. Suitable adhesives may also include those described in U.S. Pat. Nos. 4,565,783, 5,089,413, 5,681,712, and 5,232,838. In some embodiments, silicone pressure sensitive adhesives may be used, including for example those described in U.S. Pat. Nos. 7,695,818 and 7,371,464.

Despite the lack of compatibility between the materials of the microbial growth nutrient composition (e.g., being water soluble) and the adhesive composition (e.g., being water insoluble), a sufficient amount of nutrients are able to traverse through the layer of the adhesive composition to be available for microorganism consumption in the devices according to the second aspect. Moreover, due to being covered (e.g., masked) by the first adhesive composition, the nutrients are not exposed on the surface of the film and thus are protected from washing off when a fluid sample is introduced into the device. This is particularly relevant because the sample must contact the powder layer and then pass through a filter in microbial detection devices according to the present disclosure.

Figure 2:
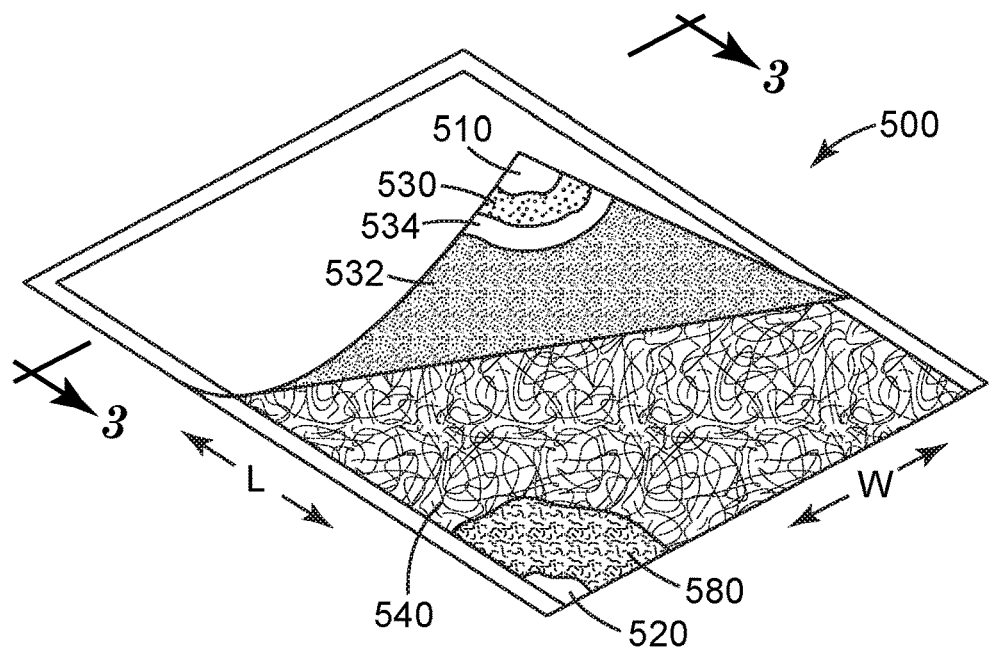
FIG. 2 is another perspective view, partially in section, of the device of FIG. 1.
Figure 11:
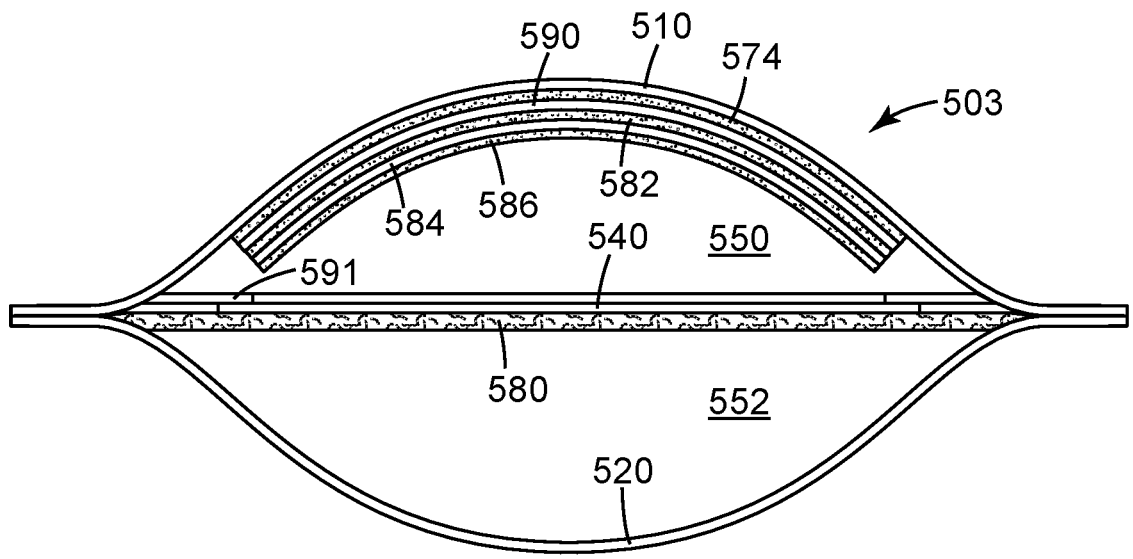
FIG. 11 is a cross-sectional view, taken along the line 11-11, of the device of FIG. 10.

Further, a dry (i.e., substantially water-free) cold-water-soluble gelling agent is adhered to the adhesive composition. For instance, FIGS. 2 and 3 show the cold-water-soluble gelling agent as a dry coating 532 disposed on the layer of adhesive composition 534, which is adhered to the layer of microbial nutrient composition 530, which is disposed on the inner surface 512 of the first wall portion 510. In addition, the pouch 55 has an absorbent pad 580 disposed in the second compartment 552. In certain embodiments, a deformable second wall portion is disposed proximate the absorbent pad 580 (not shown). In any embodiment, the dry coating may be adhered to a first substrate (e.g., adhered to an adhesive layer disposed between the cold-water-soluble gelling agent and the first wall portion) that is adhered to the first wall portion 510 of the pouch 55. This optional configuration is shown in FIG. 11 and described herein below.

Whether the cold-water-soluble gelling agent is adhered to the first wall portion of the pouch or to a first substrate that is adhered to the first wall portion, the area defined by the coating comprising the cold-water-soluble gelling agent also defines the area in which microorganisms from the sample grow and are enumerated after a sample is deposited into the first compartment. Because the device comprises an absorbent pad (described below) that absorbs most of the liquid from the sample, the cold-water-soluble gelling agent is hydrated by only a fraction of the liquid sample. Advantageously, the devices of the present disclosure use a surprisingly smaller ratio of growth area:sample volume than previously-reported thin-film culture devices.

Cold water-soluble gelling agents that are suitable for use in culture devices are known in the art and include, for example, cold-water-soluble natural and synthetic gelling agents. Natural gelling agents such as alginate, carboxymethyl cellulose, tara gum, hydroxyethyl cellulose, guar gum, locust bean gum, xanthan gum, and synthetic gelling agents such as polyacrylamide, polyurethane, polyethylene oxides, and mixtures thereof are generally suitable. Appropriate gelling agents can be selected according to the teaching of this disclosure and the disclosures of U.S. Pat. Nos. 4,565,783; 5,089,413; and 5,232,838. Other preferred gelling agents include hydroxypropyl methylcellulose; these gelling agents being useful individually, or preferably, in combination with another gelling agent such as one of the aforementioned gelling agents.

In any embodiment, the dry, cold-water soluble gelling agent can be disposed in the pouch as a dry powder adhered to an adhesive layer, as described herein. Processes and adhesives for coating a dry powder onto a flexible film for use in a thin-film culture device are described, for example, in U.S. Pat. Nos. 4,565,783; 5,089,413; and 5,232,838.

A number of thin-film culture devices are known. These devices, sold under the tradenames PETRIFILM, COMPACT DRY, and SANITA-KUN, for example. The devices typically include a gelling agent and/or water-absorptive matrix, nutrients, and chromogenic indicators to indicate presence of a microorganism colony. The thin-film culture devices typically are configured to receive one milliliter of a liquid sample, which hydrates the nutrients, indicators, and gelling agent and provide an environment for growth and enumeration of microorganism colonies. The one-milliliter sample is spread over a growth are of about 20 cm$^2$ (e.g., PETRIFILM™ Aerobic Count Plate) to about 30 cm$^2$ (e.g., PETRIFILM Yeast & Mold Count Plate). The PETRIFILM High-Sensitivity Coliform Count Plate is configured to receive 5 milliliters of sample, which is spread in the plate over an area of approximately 60 cm$^2$. Thus, previous thin-film culture devices have a growth area (that includes a gelling agent and/or water-absorptive matrix) configured to receive about 1-5 milliliters of sample and to spread the microorganisms from that sample volume over a growth area that is equal to about 12 cm$^2$ per mL of sample to about 30 cm$^2$ per mL of sample.

In contrast to previous thin-film culture devices, a device of the present disclosure is configured to receive 100-150 mL of a liquid sample and has a growth area (that includes a cold water-soluble gelling agent) of about 80 cm$^2$. Thus, the microorganisms from the 150 mL sample volume is spread over a growth area that is equivalent to less than 1 cm$^2$ per mL of sample.

The pouch 55 (i.e., at least one wall, and wall portions thereof) is fabricated of a water-proof, deformable material. In any embodiment, the deformable material may comprise a flexible, sheet-like material such as a polymeric film, for example. Suitable materials for use when fabricating the at least one wall include polyethylene, polypropylene, polyethylene terephthalate, polyamide, polyurethane, polyvinyl chloride, polyacrylate, polyurea, and combinations thereof. The at least one wall of the pouch can be relatively thin (e.g., approximately 25 microns thick) or relatively thicker (e.g., approximately 125 microns thick), provided at least a portion of the at least one wall (e.g., first wall portion 510, which is opposite the membrane filter 540 in the first compartment 550) can deform when the pouch 55 receives a liquid sample (not shown) and/or at least a portion of the at least one wall (e.g., second wall portion 520, which is proximate the absorbent pad described herein) can deform when at least a portion of the sample passes from the first compartment into the second compartment.

The membrane filter 540 permits passage of a liquid (an aqueous liquid, not shown) from the first compartment 550 to the second compartment 552 and prevents passage of particles of a predetermined size from the first compartment to the second compartment. Thus, when an aqueous liquid sample suspected of containing a target microorganism is placed into the first compartment 550, a first portion of the aqueous liquid passes (e.g., by gravity flow) through the membrane filter 540 into the second compartment 552 where it is absorbed by the absorbent pad 580. The target microorganism is trapped on or in the filter membrane 540 or is retained in a second portion of the aqueous liquid that remains in the first compartment 550.

The use of membrane filters to trap and retain microorganisms is well known in the art. Accordingly, there are a number of suitable membrane filters that can be used in a device according to the present disclosure. Nonlimiting examples of suitable membrane filters include fibrous membrane filters made of nylon, polyether sulfone, polytetrafluoroethylene, or cellulosic materials (e.g., mixed cellulose esters), microporous plastic films (e.g., laser-etched polycarbonate film), and ceramic membrane filters. It has unexpectedly been discovered that microbial detection devices according to the present disclosure having polyether sulfone membranes can contain an effective amount of sodium lauryl sulfate that inhibits growth of gram positive bacteria and/or non-coliform microorganisms while allowing gram negative bacteria such as coliform microorganisms to grow, for instance in which the effective amount is 7.43 mg sodium lauryl sulfate per 12 in$^2$ of a surface. The specific effective amount of sodium lauryl sulfate to achieve selective growth, however, may vary with the selection of the membrane material.

The porosity of the membrane filter generally is chosen so that the target microorganisms will not pass all the way though the pores from one side of the membrane filter to the other side, thereby insuring that substantially all target microorganisms in the sample are retained by the filter. Typical bacteria are about 0.5 to 5.0 micrometers (μm) in length. Certain smaller bacteria, such as *Mycoplasma* spp., are approximately 0.3 μm in diameter. Yeast cells are generally larger than bacteria. Accordingly, the selection of a membrane filter with a suitable pore size may depend upon the target microorganism. For example, a membrane filter with a nominal pore size of 1.0 μm or less, 0.8 μm or less, 0.6 μm or less, 0.4 μm or less, 0.2 μm or less, 0.1 μm or less, 0.05 μm or less, 0.03 μm or less, 0.02 μm or less, or 0.01 μm or less may be suitable to capture and detect target bacteria.

Membrane filters may be prepared manually from suitable filtration media or, alternatively, may be purchased in pre-cut sizes and shapes. The size and shape of the membrane filter can be chosen based upon the sample volume and the expected load of particulate material in the sample. In general, membrane filters with larger surface areas will allow for higher filtration rates than membrane filters with smaller surface areas. Membrane filters may be used in combination with other filtration media (e.g., a prefilter, to trap larger debris in the sample) or other membrane filters.

In any embodiment, the membrane filter may be supported (e.g., by a scrim, not shown) to provide physical stability for the membrane during use. In any embodiment, the support may be attached to the membrane filter (e.g., on the second major surface). In any embodiment, the membrane filter can comprise a wetting agent (e.g., a nonionic surfactant) to facilitate rapid and complete penetration of the liquid sample throughout the membrane filter. Preferably, the wetting agent is in an amount sufficient to facilitate wetting the membrane with an aqueous liquid, but in an amount that does not substantially inhibit growth of the target microorganism when using the device.

The dry, cold water-soluble gelling agent is hydrated and forms a hydrogel when an aqueous sample is placed into the first compartment 550 of the pouch 55. As the first portion of the aqueous liquid moves through the membrane filter 540 from the first compartment 550 to the second compartment 552, the hydrogel contacts the first surface of the membrane filter 540, thereby immobilizing any microorganisms retained on or in the membrane filter.

In any embodiment, the microbial detection device may comprise an indicator reagent disposed in the pouch for indicating microorganism growth (e.g., the presence of a viable microorganism). Often, the indicator reagent is disposed in the first compartment of the pouch. In certain embodiments, the indicator reagent is contained in an adhesive layer, a dry nutrient, and/or a cold-water-soluble gelling agent. If the indicator reagent is in the form of a powder, it may be blended with the dry nutrient or cold-water-soluble gelling agent. Alternatively, at least one component of an indicator system can be included in an aqueous liquid (e.g., water, a buffer, and/or the sample) that is deposited into or onto the microbial growth zone when the culture medium is rehydrated for use. In certain embodiments, at least one component of an indicator system may be dissolved in an organic solvent (e.g., methanol) and blended with an adhesive composition before applying an adhesive layer 534. In any embodiment, the dry coating 532 or the layer of microbial nutrient composition 530 may comprise one or more indicator reagents, either the same or different.

In certain embodiments, the indicator reagent comprises at least one of a lactose-fermentation indicator system, a redox indicator system, or a beta-D-glucuronidase indicator system. A lactose fermentation indicator system provides two indications of colonies of coliform bacteria growing in device: a first indication (acid production) due to the fermentation of lactose and a second indication (gas production) due to the fermentation of lactose. The production of both acid and gas ($CO_2$) from the fermentation of lactose confirm a presence of a colony of coliform microorganisms growing in the device. The presence of acid and gas in combination with the precipitation of the TTC reduction product 'formazan' at the point of colony growth can provide differentiation of coliform bacteria from E. coli organisms if a beta-D-glucuronidase indicator system is also present. Accordingly, the lactose fermentation indicator system comprises D-lactose and a pH indicator. The pH indicator has a transition range around 7.0. Suitable pH indicators include sulfonephthalein pH indicators such as phenol red and chlorophenol red, for example.

The lactose-fermentation indicator system further includes an inducer compound that enhances production of enzymes (e.g., beta-galactosidase) for utilizing lactose. Non-limiting examples of suitable inducer compounds include isopropyl-beta-D-thiogalactoside (IPTG), phenyl-beta-D-galactoside, methyl-beta-D-glucuronide, D-glucuronic acid, and combinations thereof.

In some embodiments, the beta-D-glucuronidase indicator system comprises 5-bromo-4-chloro-3-indolyl-beta-D-glucuronide, and at least one of methyl-beta-D-glucuronide, phenyl-beta-D-glucuronide, and D-glucuronic acid. Optionally, the lactose-fermentation indicator system comprises lactose, a pH indicator, an inducer compound, and 2,3,5-triphenyl tetrazolium chloride (TTC), as described in U.S. Pat. No. 5,409,838, which is incorporated herein by reference in its entirety. Suitable pH indicators include for instance and without limitation, pH indicators selected from the group consisting of phenol red, chlorophenol red, and combinations thereof.

The dry, rehydratable culture medium of a device according to the present disclosure optionally comprises a beta-D-glucuronidase indicator system disposed in the microbial growth zone. The beta-D-glucuronidase indicator system provides an indication of colonies, such as E. coli colonies, that produce beta-D-glucuronidase enzyme activity. Thus, the beta-D-glucuronidase indicator system provides a means of distinguishing E. coli colonies present in the device from non-E. coli-coliform colonies present in the device. Accordingly, the beta-D-glucuronidase indicator system comprises a chromogenic beta-D-glucuronidase enzyme substrate (e.g., 5-bromo-4-chloro-3-indolyl-beta-D-glucuronide). In addition, the beta-D-glucuronidase indicator system often further comprises a plurality of compounds that enhance beta-glucuronidase enzyme activity in E. coli. Non-limiting examples of suitable compounds that enhance beta-glucuronidase enzyme activity in E. coli include methyl-beta-D-glucuronide, phenyl-beta-D-glucuronide, and D-glucuronic acid. In any embodiment, a first compound that enhances beta-glucuronidase enzyme activity in E. coli is selected from methyl-beta-D-glucuronide and phenyl-beta-D-glucuronide. In any embodiment, a second compound that enhances beta-glucuronidase enzyme activity in E. coli is D-glucuronic acid. Surprisingly, a device having a combination of first and second compounds that enhances beta-glucuronidase enzyme activity in E. coli has been found to better able to detect beta-glucuronidase-positive E. coli.

Without being bound by theory, it is believed that at least one of the plurality of compounds that enhance beta-glucuronidase enzyme activity in E. coli may induce the production of more beta-glucuronidase enzyme by the cells. Alternatively, or additionally, at least one of the plurality of compounds that enhance beta-glucuronidase enzyme activity in E. coli may enhance the activity of the beta-glucuronidase enzyme molecules when they react with a chromogenic enzyme substrate (e.g., 5-bromo-4-chloro-3-indolyl-beta-D-glucuronide).

The indicator reagent may be a first indicator reagent and the microbial detection device may further comprise a second indicator reagent. In any such embodiments, the first indicator reagent may be a beta-D-glucuronidase substrate and the second indicator reagent may be a beta-D-galactosidase substrate. In some embodiments, the first indicator reagent is 2,3,5-triphenyl tetrazolium chloride, a pH indicator, or a beta-D-galactosidase substrate, and the second indicator reagent is a glucuronidase substrate selected from the group consisting of p-nitrophenyl-beta-glucuronide, p-nitrophenyl-2,3,4-tri-O-acetyl-beta-glucuronic acid methyl ester, phenolphthalein glucuronic acid, phenolphthalein mono-P-glucuronic acid, naphthyl-AS-BI-beta-D-glucuronide, 4-methylumbelliferyl-beta-D-glucuronide, sodium salt of 8-Hydroxyquinoline-beta-D-glucuronic acid, sodium salt of 2-Naphthyl-beta-D-glucuronic acid, sodium salt of 4-Nitrophenyl-beta-D-glucuronic acid, sodium salt monohydrate of Phenolphthalein-beta-D-glucuronic acid, cyclohexylammonium salt of 5-Bromo-4-chloro-3-indoxyl-beta-D-glucuronic acid, cyclohexylammonium salt of 3-Indoxyl-beta-D-glucuronic acid, sodium salt of 3-Indoxyl-beta-D-glucuronic acid, cyclohexylammonium salt of 5-Bromo-6-chloro-3-indoxyl-beta-D-glucuronic acid, anhydrous sodium salt of 5-Bromo-4-chloro-3-indoxyl-beta-D-glucuronic acid, and sodium salt trihydrate of 5-Bromo-4-chloro-3-indoxyl-beta-D-glucuronic acid. In select embodiments, the second indicator reagent is preferably sodium salt trihydrate of 5-Bromo-4-chloro-3-indoxyl-beta-D-glucuronic acid.

In any embodiment, a device of the present disclosure typically comprises an effective amount of one or more dry nutrient (e.g., a nutrient medium selected to support growth of the target microorganism). The one or more dry nutrient may be disposed in the first compartment, for example. In any embodiment, the one or more dry nutrient may be disposed in the device (e.g., in the first compartment) as a dry powder or agglomerated powder. In any embodiment, the one or more nutrient can be adhered to the pouch (e.g., adhered to an inner surface of the first wall portion in the first compartment). In any embodiment, the one or more nutrient may be adhered to an adhesive layer that is adhered to an inner surface the first wall portion, as described herein for the dry, cold water-soluble gelling agent.

Suitable microbial growth nutrient compositions typically comprise for instance and without limitation one or more nutrients including a meat peptone, a casein peptone, a gelatin peptone, a soy peptone, a beef extract, a yeast extract, lactose, glucose, dextrose, tryptose, galactose, tryptone, a fat, a mineral, or a vitamin. Further, non-limiting examples of nutrients, additional gelling agents, and mixtures thereof for supporting growth of microorganisms in a device of the present disclosure include those described in U.S. Pat. Nos. 4,565,783; 5,089,413; 5,232,838; 5,364,766; 5,443,963; 5,462,860; 5,601,998; 5,635,367; and 5,681,712; these references also include non-limiting examples of indicator agents (e.g., detection reagents) and inducers.

In any embodiment, a device of the present disclosure can comprise a reagent for buffering the culture medium when the culture medium is reconstituted with an aqueous liquid during use. The reagent can buffer the culture medium (when hydrated during use) at a pH between about 6.5 and 7.5. A non-limiting example of a suitable reagent for buffering the culture medium a phosphate salt (e.g., $Na_2HPO_4$, $NaH_2PO_4$, $K_2HPO_4$, $KH_2PO_4$, or a combination of any two or more of the foregoing reagents). The reagent is disposed (e.g., in the dry, rehydratable culture medium) in the microbial growth zone of the culture device.

In any embodiment, it may be desirable to incorporate a non-specific indicator (e.g., a dye) into the microbial growth zone in order to indicate a presence of a microbial colony growing in the device. In some embodiments, the indicator may be incorporated into the culture medium. Alternatively, the indicator may be incorporated in the adhesive. Suitable indicators are those which are metabolized by growing microorganisms, and which cause the colonies to be colored for easier visualization. Examples of such non-specific indicators include triphenyl tetrazolium chloride, p-tolyl tetrazolium red, tetrazolium violet, veratryl tetrazolium blue, and related dyes. Any one or more of the preceding non-specific indicators can be used in combinations.

Before a liquid sample is deposited into the pouch, the absorbent pad 580 is preferably relatively thin (e.g., less than or equal to 5 mm thick, less than or equal to 4 mm thick, less than or equal to 3 mm thick, less than or equal to 2 mm thick, less than or equal to about 1 mm thick) and is configured to absorb a quantity of deionized water equal to many time its own weight (e.g., at least 100-times its own weight, at least 150-times its own weight, at least 200-times its own weight, at least 250-times its own weight, at least 300-times its own weight, at least 350-times its own weight, at least 400-times its own weight, at least 500-times its own weight). In any embodiment, the absorbent pad may comprise a plurality of materials such as, for example, a super-absorbent material (e.g., a superabsorbent polymer; "herein, "SAP") and a less-absorbent or nonabsorbent carrier (e.g., cellulosic fibers). A nonlimiting example of a suitable absorbent pad is a composite polyacrylate laminate structure comprising a superabsorbent polymer granule base disposed between two cellulose sheets. In any embodiment of the absorbent pad, the pad may comprise SAP granules disposed in an air-laid nonwoven material or SAP fibers blended with carrier fibers into a nonwoven material.

Optionally, in any embodiment (not shown), the absorbent pad may be coupled to a component of the pouch (e.g., the second wall portion) in the second compartment. Advantageously, this can keep the pad from deforming (e.g., as it swells with liquid migrating from the first compartment) to an extent that it loses contact with a substantial portion of the membrane filter. The pad may be coupled to the pouch via an adhesive (e.g., a pressure-sensitive adhesive), a thermal weld or other suitable attachment means known in the art. In any embodiment, the absorbent pad may be releasably coupled to the pouch (e.g., by a water-soluble gum). This embodiment holds the pad in a proper position to receive liquid passing through the membrane filter, but permits lateral movement of the pad as it swells due to absorption of a large quantity of the liquid.

Referring back to the drawings, FIG. 5 shows one embodiment of a sealable sample port 560 of a device 501 according to the present disclosure. The device 501 comprises a pouch 55 having a first wall portion 510, a second wall portion 520, and a sealable sample port 560 consisting of an opening, each as described herein. An inner surface of the first wall portion 510 comprises an adhesive strip 516 coated thereon along the edge of the inner surface proximate the opening. Adhered to the adhesive strip 516 is a release liner 518. After the sample is deposited (e.g., by pouring or pipetting) into the first compartment (not shown in FIG. 5) through the opening (sample port 560), the operator removes the release liner and contacts the adhesive strip 516 (e.g., a pressure-sensitive adhesive) with an inner surface of the second wall portion 520 proximate the opening in order to seal the opening. Optionally, the operator can expel (out of the opening) some or all of the air from the first compartment when completing the sealing process.

FIG. 6 shows an alternative embodiment of a device 502 comprising a pouch 56 comprising a sealable sample port 560 with an opening 561. In this embodiment, the sealable sample port 560 is a screw-cap opening into which the liquid test sample cab be poured or pipetted, for example. Alternatively, in any embodiment, the sealable sample port 560 can be a pierceable, elastically-deformable septum through which a needle or a pipet tip can be introduced to deliver the sample into the first compartment. After the needle or pipet is withdrawn from the septum, the elastically-deformable septum reseals the port. Advantageously, in these embodiments, the introduction of air into the first compartment can be minimized.

In another alternative embodiment (not shown), the sealable sample port can comprise interlocking zipper components (e.g., similar to a ZIPLOK® plastic storage bag) on each of the first wall portion and second wall portion and a zipper component that is used cooperatively with the interlocking components to open or seal the first compartment.

Figure 7:
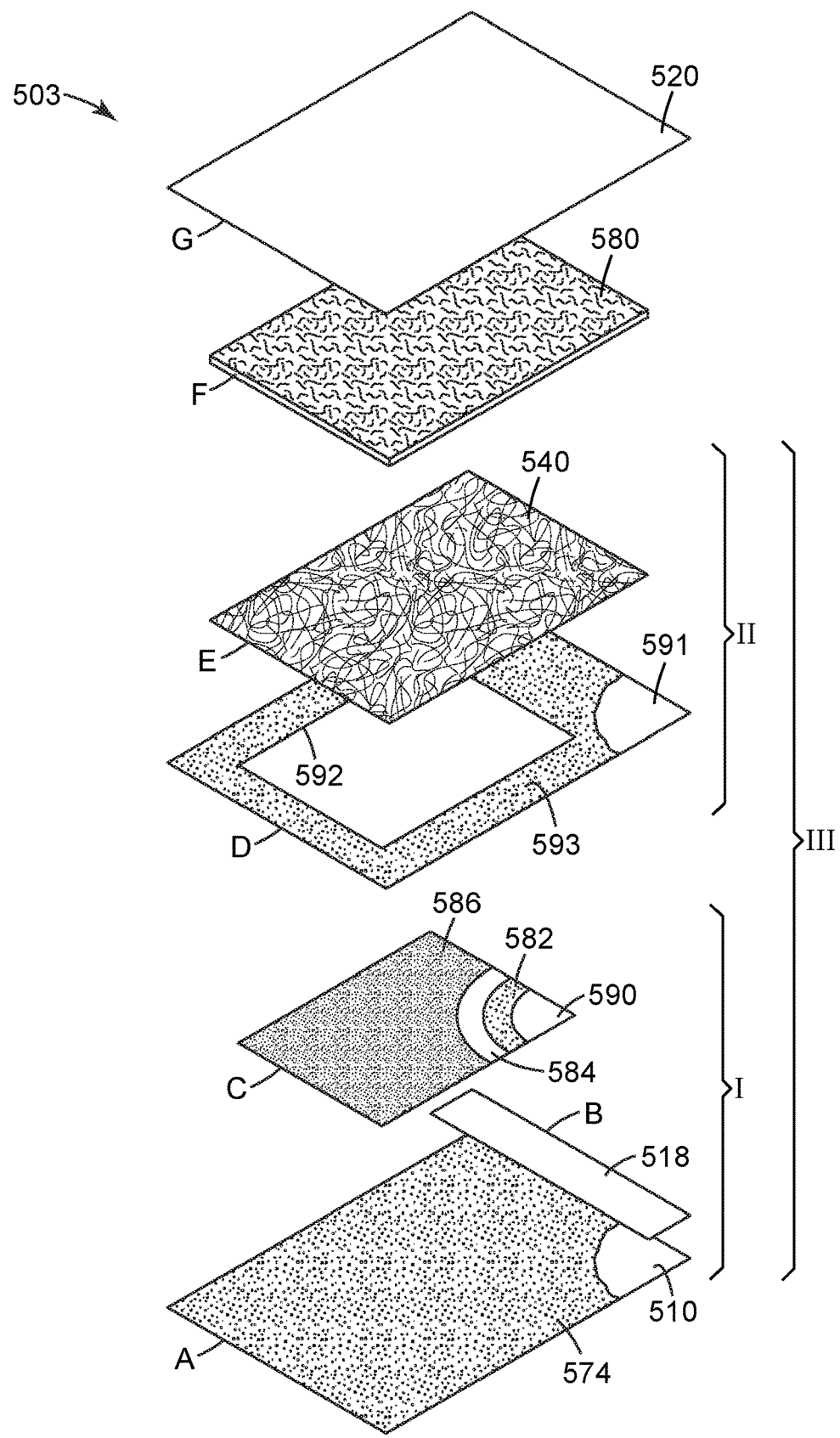
FIG. 7 is an exploded view of another alternative embodiment of a device according to the present disclosure.
Figure 8:
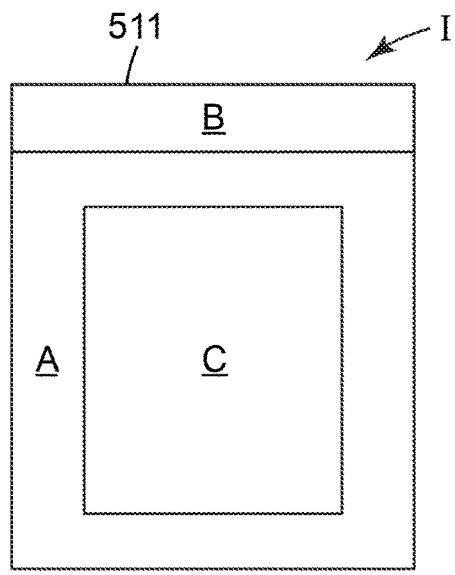
FIG. 8 is a first subassembly of the device of FIG. 7.
Figure 9:
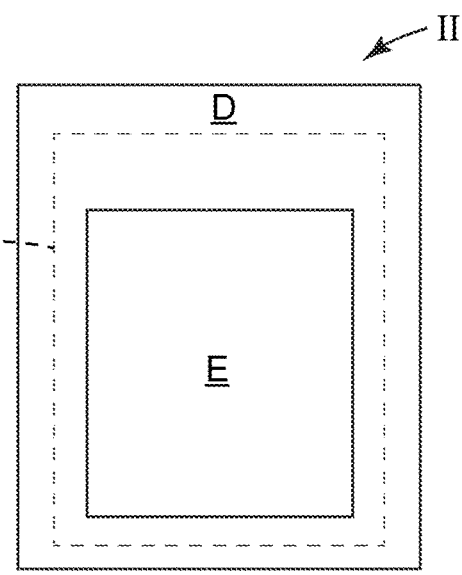
FIG. 9 is a second subassembly of the device of FIG. 7.

The present disclosure provides a method of assembling a large-volume, thin-film culture device. Devices of the present disclosure can be assembled entirely from sheet-like materials. Advantageously, this enables the use of roll-to-roll processes when assembling a plurality of devices. FIGS. 7-9 show various views of an alternative embodiment of a device 503 according to the present disclosure.

FIG. 7 shows the sheet-like materials that are used to assemble one embodiment of a device according to the present disclosure. Each part of the device can be cut into appropriately-sized sheets and subsequently assembled into the device or, alternatively can be cut to the appropriate size using controlled-depth die cutting using a roll-to-roll process known in the art.

In any embodiment, a device of the present disclosure can be partially assembled into one or more subassembly, which is subsequently combined with other components to make the device. Referring to FIG. 7, the device 503 includes a first subassembly I that comprises a first part A, a second part B, and a third part C. Another view of the assembled first subassembly I is shown in FIG. 8. The first part A consists of the first wall portion 510 with an adhesive layer 574 coated thereon as described herein. Second part B consists of a release liner 518 as described herein. Third part C consists of a first substrate 590 coated on one side with a substantially dry microbial growth nutrient composition 582. Adhered to the microbial growth nutrient composition 582 is an adhesive layer 584. Disposed on the adhesive layer 584 is a coating 586 that comprises the dry, cold-water-soluble gelling agent described herein. The coating 586 can be deposited onto the adhesive layer 586 as a dry powder or as a liquid composition that is subsequently dried to a substantially water-free state, as described hereinabove. The first substrate 590 can comprise a sheet-like material similar to those used for the walls of the pouch as described above. Alternatively, the first substrate can comprise a nonwoven fabric or a cellulosic material (e.g., paper). In any embodiment, the cellulosic material can be coated with a waterproof coating that is substantially noninhibitory to growth of microorganisms. The area defined by the coating 584 on third part C also defines the growth and colony-enumeration area in the assembled device.

When assembling subassembly I, the release liner 518 is releasably adhered to the adhesive layer 574 along the edge (edge 511) of the first wall portion 510 that forms the opening of the assembled device. In addition, the third part C is positioned centrally over part A with the coating 586 facing away from the adhesive layer 574. Part C is then contacted with adhesive 574 to affix part C to part A with the coating 586 exposed, as shown in FIG. 8.

Referring back to FIG. 7, a second subassembly II includes a fourth part D and a fifth part E. The fourth part D comprises a second substrate 591. The second substrate 591 forms a frame comprising an aperture 592. The second substrate 591 is coated on one side with an adhesive layer 593. The second substrate 591 can comprise a sheet-like material (e.g., a flexible film) similar to those used for the walls of the pouch as described above. Alternatively, the second substrate can comprise a nonwoven fabric or a cellulosic material (e.g., paper). In any embodiment, the cellulosic material can be coated with a waterproof coating that is substantially noninhibitory to growth of microorganisms. Optionally, the absorbent pad can be coupled to the second substrate in the second compartment.

The second subassembly II also includes the fifth part E (i.e., membrane filter 540, as described herein). The membrane filter 540 is dimensioned so that it completely covers the area defined by the aperture 592. When assembling subassembly II, the membrane filter 540 is adhered to the adhesive layer 593 so that it completely covers the aperture 592 of the second substrate 591, as shown in FIG. 9. In use, liquid passes through the aperture from the first compartment to the second compartment of the device as the liquid passes through the membrane filter. In any embodiment, the aperture 592 defines a first area and the coating 584 defines a second area. Preferably, the second area is greater than or equal to the first area. More preferably, the second area is shaped and dimensioned to completely overlap the area of the aperture.

Optionally, when assembling the device 503 of FIG. 7, the subassembly I can be coupled to subassembly II to form a subassembly III. This can be done by placing the back side (i.e., the side that does not include adhesive layer 593) of subassembly II in overlaying contact with the adhesive-coated side of subassembly I. In addition, the aperture 592 of subassembly II is aligned with subassembly I so that it overlaps the third part C of subassembly I.

Figure 10:
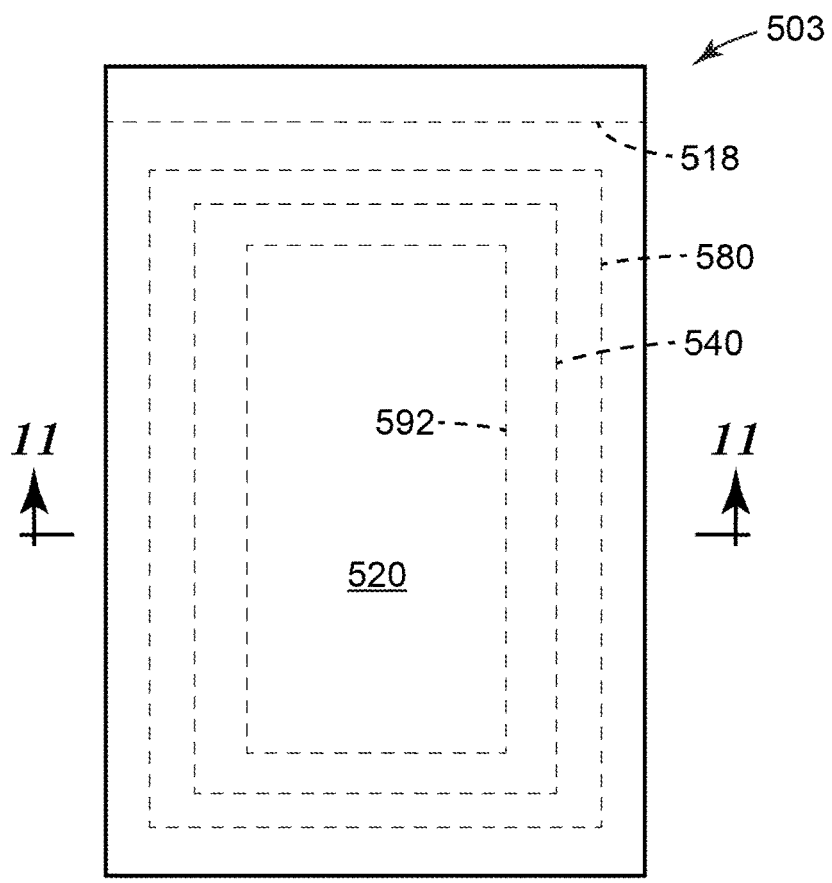
FIG. 10 is a plan view of the assembled device of FIG. 7.

To complete the construction of the device 503, the sixth part F (i.e., absorbent pad 580, as described herein) is placed in overlaying contact with the membrane filter 540 of the subassembly III and the seventh part (i.e., second wall portion 520, as described herein) is placed in overlaying contact with the first part A such that the seventh part G is adhesively coupled to the portion of the adhesive layer 574 at the periphery of the first part A. FIG. 10 shows a plan view and FIG. 11 shows a cross-sectional view of the assembled device 503 of FIG. 7.

In any embodiment of a device according to the present disclosure, the device further comprises a stand-off layer (not shown) disposed in the second compartment between the membrane filter and the absorbent pad. The stand-off layer is a relatively-thin (e.g., about 0.1 mm to 2 mm thick) sheet-like material. In any embodiment, the stand-off layer is shaped and dimensioned to be at least coextensive with the membrane filter. In any embodiment, the stand-off layer is substantially less absorbent than the absorbent pad. In any embodiment, the absorbency of the stand-off layer is less than or equal to the absorbency of the membrane filter. The stand-off layer may comprise or consist essentially of a hydrophobic material (e.g., unmodified polypropylene).

The stand-off layer functions to permit the passage of aqueous liquid from the membrane filter to the absorbent layer during the initial period in which over half of the aqueous liquid deposited into the first compartment passes into the second compartment, while restricting diffusion of nutrient from the first compartment to the second compartment while the device is being incubated to facilitate microbial colony growth.

Suitable materials for use as the stand-off layer include, for example nonwoven fabrics comprising polypropylene; polyethylene; polyethylene terephthalate; a blend of polyethylene terephthalate and cellulose; a blend of polyethylene terephthalate and rayon; and mixtures thereof. Advantageously, devices comprising the stand-off layer can include dry nutrients coated on the first wall portion of the pouch and can retain enough nutrients in the hydrated cold water-soluble gelling agent to support growth of the target microorganisms in the hydrated nutrient gel.

In another aspect, the present disclosure provides a method. More particularly, the method comprises:
    placing a predetermined volume of aqueous sample into the first compartment of the microbial detection device of any of the preceding embodiments;
    sealing the sample port;
    incubating the device for a period of time at a temperature that facilitates growth and detection of a target microorganism; and
    detecting a presence or an absence of a colony of the target microorganism in the device.

Figure 12:
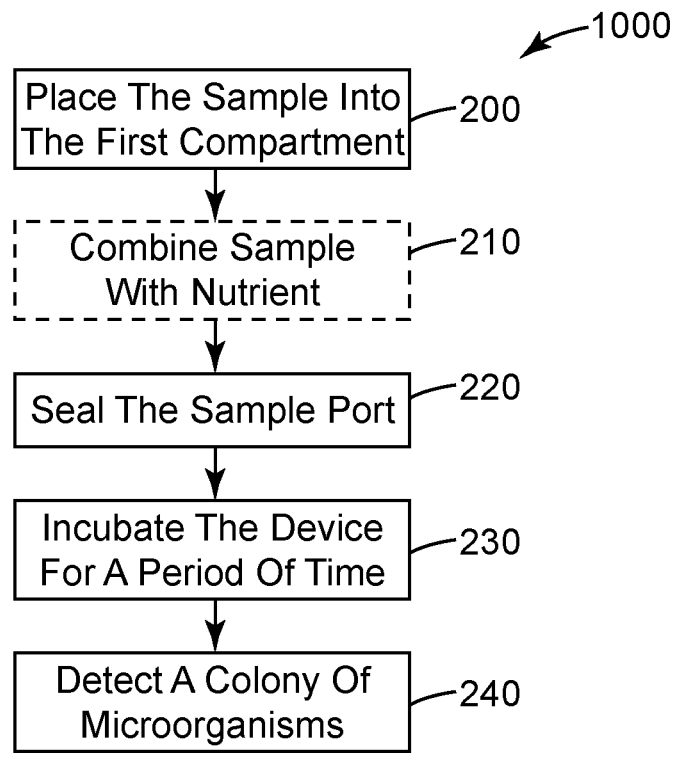
FIG. 12 is a block diagram of one embodiment of a method of detecting a target microorganism according to the present disclosure.

The method can be used to detect and, optionally, enumerate target microorganisms in a liquid sample. FIG. 12 shows a block diagram that shows the steps of one embodiment of a method 1000 of detecting microorganisms in a liquid sample according to the present disclosure.

The method 1000 comprises a step 200 of placing a predetermined volume of aqueous sample into the first compartment of the device of any one of the embodiments of the present disclosure. The aqueous sample can be any filterable liquid sample to be tested for presence of a target microorganism. The method is particularly useful for water samples that are suspected of containing relatively low concentrations (e.g., less than or equal to 10 microorganisms per milliliter, less than or equal to 1 microorganism per milliliter, less than or equal to 0.1 microorganisms per milliliter, less than or equal to 0.01 microorganism per milliliter,) of target microorganisms. Placing a predetermined volume of aqueous sample into the first compartment of the device comprises placing the predetermined volume into the device (e.g., via pipetting, pouring, injecting, or the like) through the sealable sample port.

The method 1000 further comprises a step 210 of sealing the sample port. The procedure for sealing the sample port will depend upon the particular sealable sample port that is present in the device used in the method 1000. For example, if the device 503 of FIGS. 10-11 is used in the method, sealing the sample port comprises removing the release liner 18 to expose an adhesive disposed on the first wall portion 10 and then contacting the adhesive on the first wall portion with the second wall portion to form a waterproof seal that closes the opening of the pouch.

For example, if the device 502 of FIG. 6 is used in the method 1000, sealing the sample port comprises screwing the cap back onto the sample port, thereby forming a waterproof seal.

For example, if a device comprising an elastically-deformable pierceable septum (not shown) is used in the method 1000, sealing the sample port will spontaneously occur as the pipet or needle used to introduce the sample into the device is withdrawn from the septum.

In any embodiment of the method, air may be expelled (e.g., manually, by squeezing) from the pouch via the sealable sample port before and or during the process of forming the waterproof seal.

The method 1000 further comprises a step 220 of incubating the device for a period of time at a temperature that facilitates growth and detection of a target microorganism. A person having ordinary skill in the art will recognize the incubation temperature and period of time will depend upon a number of factors (e.g., the target microorganism, nutrients present in the sample, nutrients present in the device, inhibitory agents present in the sample and/or the device) and will adjust the incubation time and temperature accordingly.

The method 1000 further comprises a step 230 of detecting a presence or an absence of a colony of the target microorganism in the device. In any embodiment, detecting a presence or an absence of a colony of the target microorganism in the device can comprise detecting a colony (e.g., visually or using machine vision) in the first compartment of the device. In any embodiment, detecting a presence or an absence of a colony of the target microorganism (e.g., Gram negative bacteria) in the device can comprise detecting a change associated with the indicator reagent. The indicator reagent may change from a first state (e.g., substantially colorless or nonfluorescent) to a second state (e.g., colored or fluorescent) in and/or surrounding a colony of the target microorganism. When the aqueous sample contains at least one coliform, the detecting may comprise detecting a colony of the one or more coliforms. Likewise, when the aqueous sample contains at least one strain of *Escherichia coli*, the detecting preferably comprises detecting a colony of the one or more strains of *Escherichia coli*.

In any embodiment, the colonies can be enumerated (e.g., counted) and, optionally, the number of colonies of target microorganisms can be recorded. Advantageously, in certain embodiments when the aqueous sample contains both Gram negative bacteria and Gram positive bacteria, the method may further comprise counting Gram negative bacteria colonies separately from Gram positive bacteria colonies.

In any embodiment, after sealing the sample port, the method further comprises laying the outer surface of the first wall portion of the device or laying the outer surface of the second wall portion of the device onto a surface that is substantially perpendicular to gravitational force. Advantageously, laying the outer surface of its second wall portion of the device onto a surface that is substantially perpendicular to the force of gravity facilitates flow of the sample liquid through the membrane filter by force of gravity. In addition, laying the outer surface of its second wall portion of the device onto a surface that is substantially perpendicular to the force of gravity facilitates contact between the hydrated cold water-soluble gelling agent adhered to the first wall portion and the membrane filter as the liquid passes through the membrane filter from the first compartment to the second compartment.

In any embodiment, the method further comprises passing at least 90%, at least 92%, at least 95%, at least 97% or at least 98% of the predetermined volume from the first compartment to the second compartment, e.g., by gravity force and/or capillary force. The portion of the predetermined volume that remains in the first compartment is substantially present as part of the gel formed by hydrating the cold water-soluble gelling agent.

In any embodiment, the method further comprises a step 240 of combining the aqueous sample with a nutrient, nutrient medium, indicator reagent and/or selective agent prior to placing the predetermined volume into the first compartment. In any embodiment, the method further comprises combining the aqueous sample with a nutrient, nutrient medium, indicator reagent and/or selective agent after placing the predetermined volume into the first compartment.

EXEMPLARY EMBODIMENTS

Embodiment 1 is a microbial detection device. The microbial detection device includes:
  a water-proof pouch comprising:
    a first wall portion having an inner surface and an outer surface;
    a second wall portion having an inner surface and an outer surface;
    a porous membrane filter disposed in the pouch between the inner surface of the first wall portion and the inner surface of the second wall portion, the membrane filter having a first major surface and a second major surface opposite the first major surface;
    a first compartment defined in part by inner surface of the first wall portion and defined in part by the first major surface of the membrane filter;
    a sealable sample port that provides access to deposit a liquid into the first compartment;
    an effective amount of a dry nutrient disposed in the first compartment, the dry nutrient containing sodium lauryl sulfate in an amount of 1.75 milligrams (mg) or greater per 12 square inches (in²) of the inner surface of the first wall portion;

a second compartment defined in part by the inner surface of the second wall portion and defined in part by the second major surface of the membrane filter; wherein the membrane filter permits passage of aqueous liquids from the first compartment to the second compartment and prevents passage of particles of a predetermined size from the first compartment to the second compartment;

a dry cold water-soluble gelling agent adhered to the pouch in the first compartment; and an absorbent pad disposed in the second compartment.

Embodiment 2 is the microbial detection device of embodiment 1, further including an indicator reagent for indicating a presence of a viable microorganism, wherein the indicator reagent is disposed in the pouch.

Embodiment 3 is the microbial detection device of embodiment 2, wherein the indicator reagent is disposed in the first compartment.

Embodiment 4 is the microbial detection device of any of embodiments 1 to 3, including at least one of a lactose-fermentation indicator system, a redox indicator system, or a beta-D-glucuronidase indicator system.

Embodiment 5 is the microbial detection device of embodiment 4, wherein the lactose-fermentation indicator system includes lactose, a pH indicator, an inducer compound, and 2,3,5-triphenyl tetrazolium chloride (TTC).

Embodiment 6 is the microbial detection device of embodiment 4 or embodiment 5, wherein the beta-D-glucuronidase indicator system includes 5-bromo-4-chloro-3-indolyl-beta-D-glucuronide, and at least one of methyl-beta-D-glucuronide, phenyl-beta-D-glucuronide, and D-glucuronic acid.

Embodiment 7 is the microbial detection device of any of embodiments 2 to 4, wherein the indicator reagent includes a pH indicator selected from the group consisting of phenol red, chlorophenol red, and combinations thereof.

Embodiment 8 is the microbial detection device of any of embodiments 2 to 7, wherein the indicator reagent is a first indicator reagent and wherein the microbial detection device further includes a second indicator reagent.

Embodiment 9 is the microbial detection device of embodiment 8, wherein the first indicator reagent is a beta-D-glucuronidase substrate and the second indicator reagent is a beta-D-galactosidase substrate.

Embodiment 10 is the microbial detection device of any of embodiments 2 to 9, wherein the first indicator reagent is 2,3,5-triphenyl tetrazolium chloride, a pH indicator, or a beta-D-galactosidase substrate, and the second indicator reagent is a glucuronidase substrate selected from the group consisting of p-nitrophenyl-beta-glucuronide, p-nitrophenyl-2,3,4-tri-O-acetyl-beta-glucuronic acid methyl ester, phenolphthalein glucuronic acid, phenolphthalein mono-P-glucuronic acid, naphthyl-AS-BI-beta-D-glucuronide, 4-methylumbelliferyl-beta-D-glucuronide, sodium salt of 8-Hydroxyquinoline-beta-D-glucuronic acid, sodium salt of 2-Naphthyl-beta-D-glucuronic acid, sodium salt of 4-Nitrophenyl-beta-D-glucuronic acid, sodium salt monohydrate of Phenolphthalein-beta-D-glucuronic acid, cyclohexylammonium salt of 5-Bromo-4-chloro-3-indoxyl-beta-D-glucuronic acid, cyclohexylammonium salt of 3-Indoxyl-beta-D-glucuronic acid, sodium salt of 3-Indoxyl-beta-D-glucuronic acid, cyclohexylammonium salt of 5-Bromo-6-chloro-3-indoxyl-beta-D-glucuronic acid, anhydrous sodium salt of 5-Bromo-4-chloro-3-indoxyl-beta-D-glucuronic acid, and sodium salt trihydrate of 5-Bromo-4-chloro-3-indoxyl-beta-D-glucuronic-acid.

Embodiment 11 is the microbial detection device of embodiment 10, wherein the second indicator reagent is sodium salt trihydrate of 5-Bromo-4-chloro-3-indoxyl-beta-D-glucuronic acid.

Embodiment 12 is the microbial detection device of embodiment 10, further including an inducer disposed in the first compartment, wherein the inducer is selected from the group consisting of isopropyl-beta-D-thiogalactoside (IPTG), phenyl-beta-D-galactoside, methyl-beta-D-glucuronide, D-glucuronic acid, and combinations thereof.

Embodiment 13 is the microbial detection device of any of embodiments 1 to 12, further including a non-specific indicator selected from p-tolyl tetrazolium red, tetrazolium violet, veratryl tetrazolium blue, and combinations thereof.

Embodiment 14 is the microbial detection device of any of embodiments 1 to 13, wherein the dry nutrient contains 3.5 mg or greater sodium lauryl sulfate per 12 in² of the inner surface of the first wall portion.

Embodiment 15 is the microbial detection device of any of embodiments 1 to 14, wherein the dry nutrient contains 6.7 mg or greater sodium lauryl sulfate per 12 in² of the inner surface of the first wall portion.

Embodiment 16 is the microbial detection device of any of embodiments 1 to 15, wherein the membrane filter comprises polyether sulfone.

Embodiment 17 is the microbial detection device of any of embodiments 1 to 16, wherein the pouch contains a deformable first wall portion disposed opposite the membrane filter in the first compartment.

Embodiment 18 is the microbial detection device of embodiment 17, wherein the dry cold water-soluble gelling agent is adhered to the first wall portion.

Embodiment 19 is the microbial detection device of embodiment 18, wherein the device further includes an adhesive layer disposed between the dry cold water-soluble gelling agent and the first wall portion.

Embodiment 20 is the microbial detection device of embodiment 19, as dependent upon embodiment 2 or embodiment 3, wherein the indicator reagent is disposed on or in the adhesive layer.

Embodiment 21 is the microbial detection device of any of the preceding embodiments, wherein the pouch comprises a deformable second wall portion disposed proximate the absorbent pad in the second compartment.

Embodiment 22 is the microbial detection device of any of the preceding embodiments, wherein the membrane filter is coupled to a frame, wherein the frame includes an aperture through which liquid passes from the first compartment through the membrane filter.

Embodiment 23 is the microbial detection device of embodiment 22, wherein the aperture defines a first area, wherein the dry cold water-soluble gelling agent adhered to the pouch defines a second area that is greater than or equal to the first area.

Embodiment 24 is the microbial detection device of any of the preceding embodiments, wherein the dry cold water-soluble gelling agent adhered to the pouch defines a second area, wherein the first compartment is configured to receive a predetermined volume of about 100 mL to about 150 mL, wherein the second area defines a colony enumeration area, wherein a ratio of the predetermined volume to the colony enumeration area is less than 1 cm² per mL.

Embodiment 25 is the microbial detection device of any of the preceding embodiments, wherein the dry nutrient comprises at least one of meat peptone, casein peptone, beef extract, lactose, glucose, or galactose.

Embodiment 26 is the microbial detection device of any of the preceding embodiments, wherein the absorbent pad includes a superabsorbent polymer.

Embodiment 27 is the microbial detection device of any of the preceding embodiments, wherein the membrane filter includes a supported membrane.

Embodiment 28 is the microbial detection device of any of the preceding embodiments, wherein the membrane filter includes a wetting agent.

Embodiment 29 is the microbial detection device of any of the preceding embodiments, wherein the first wall portion is fabricated from a sheet-like flexible film.

Embodiment 30 is the microbial detection device of any of the preceding embodiments, wherein the second wall portion is fabricated from a sheet-like flexible film.

Embodiment 31 is the microbial detection device of any of embodiments 22 through 30, wherein the frame is fabricated from a sheet-like flexible film.

Embodiment 32 is the microbial detection device of any of embodiments 21 through 31, wherein the absorbent pad is coupled to the second wall portion.

Embodiment 33 is the microbial detection device of any of embodiments 22 through 32, wherein the absorbent pad is coupled to the frame.

Embodiment 34 is the microbial detection device of any of the preceding embodiments, wherein the device is dimensioned to receive a liquid sample having a volume between 25 mL and 150 mL, inclusive.

Embodiment 35 is the microbial detection device of any of the preceding embodiments, wherein the sealable sample port includes a pressure-sensitive adhesive disposed therein.

Embodiment 36 is the microbial detection device of embodiment 35, further including a release liner removably adhered to the adhesive.

Embodiment 37 is the microbial detection device of any of the preceding embodiments, wherein the dry cold water-soluble gelling agent is selected from the group consisting of alginate, carboxymethyl cellulose, tara gum, hydroxyethyl cellulose, hydroxypropyl methylcellulose, guar gum, locust bean gum, xanthan gum, polyacrylamide, polyurethane, polyethylene oxides, and mixtures of any two or more of the foregoing gelling agents.

Embodiment 38 is the microbial detection device of any of the preceding embodiments, further including a stand-off layer disposed in the second compartment between the membrane filter and the absorbent pad.

Embodiment 39 is the microbial detection device of any of the preceding embodiments, wherein the dry nutrient is present in a coat weight of 50 to 550 mg per 24 in$^2$ adhered to the first wall or to the second wall of the first compartment.

Embodiment 40 is the microbial detection device of any of the preceding embodiments, wherein the dry nutrient is present in a coat weight of 250 to 500 mg per 24 in$^2$ adhered to the first wall or to the second wall of the first compartment.

Embodiment 41 is a method. The method includes:
placing a predetermined volume of aqueous sample into the first compartment of the microbial detection device of any of the preceding embodiments;
sealing the sample port;
incubating the device for a period of time at a temperature that facilitates growth and detection of a target microorganism; and
detecting a presence or an absence of a colony of the target microorganism in the device.

Embodiment 42 is the method of embodiment 41, further including laying the outer surface of the first wall portion of the device or laying the outer surface of the second wall portion of the device onto a surface that is substantially perpendicular to gravitational force.

Embodiment 43 is the method of embodiment 41 or embodiment 42, further including passing at least 90% of the predetermined volume from the first compartment to the second compartment.

Embodiment 44 is the method of embodiment 43, wherein passing at least 90% of the predetermined volume includes passing the volume by gravity force and/or capillary force.

Embodiment 45 is the method of any of embodiments 41 through 44, further including bringing a dry cold water-soluble gelling agent into contact with the membrane filter.

Embodiment 46 is the method of any of embodiments 41 through 45, further including the step of combining the aqueous sample with a nutrient, nutrient medium, indicator reagent and/or selective agent prior to placing the predetermined volume into the first compartment.

Embodiment 47 is the method of any of embodiments 41 through 46, further including the step of combining the aqueous sample with a nutrient, nutrient medium, indicator reagent and/or selective agent after placing the predetermined volume into the first compartment.

Embodiment 48 is the method of any one of embodiments 41 through 47, further including counting microbial colonies in the device.

Embodiment 49 is the method of any of embodiments 41 through 48, wherein the aqueous sample contains Gram negative bacteria.

Embodiment 50 is the method of embodiment 49, wherein the aqueous sample further contains Gram positive bacteria; and wherein the method further includes counting Gram negative bacteria colonies separately from Gram positive bacteria colonies.

Embodiment 51 is the method of embodiment 49 or embodiment 50, wherein the aqueous sample contains at least one coliform; and wherein the detecting includes detecting a colony of the at least one coliforms.

Embodiment 52 is the method of any of embodiments 49 to 51, wherein the aqueous sample contains at least one strain of *Escherichia coli*; and wherein the detecting includes detecting a colony of the at least one strain of *Escherichia coli*.

Advantages and embodiments of this disclosure are further illustrated by the following examples, but the particular materials and amounts thereof recited in these examples, as well as other conditions and details, should not be construed to unduly limit this disclosure. All materials are commercially available or known to those skilled in the art unless otherwise stated or apparent.

EXAMPLES

Reagents

Sodium lauryl sulfate was obtained from TCI America, Portland, OR.

5-Bromo-4-chloro-3-indoxyl-beta-D-glucuronic acid, sodium salt trihydrate (BCIG) was obtained from Biosynth International Inc., Itasca, IL.

O-methyl-beta-D-glucuronide was obtained from Biosynth International Inc.

6-chloro-3-indoxyl-beta-D-galactopyranoside was obtained from Biosynth International Inc.

Isopropyl Beta-D-1-thiogalactopyranoside (IPTG) was obtained from Biosynth International Inc.

Tryptic soy broth (TSB) was obtained from Becton, Dickinson and Company, Franklin Lakes, NJ.

Deionized water was purified using a MILLI-Q water purification system (EMD Millipore, Burlington, MA).

Bacterial Strains

The bacterial strains listed in Table 1 were obtained from Microbiologics Incorporated (St. Cloud, MN) and individually incubated overnight in tryptic soy broth at 37° C. and 200 rpm in an INNOVA44 incubator (New Brunswick Scientific, Enfield, CT). Individual inoculums were prepared by serially diluting each culture sample with Butterfield's Buffer (3 M Corporation, Maplewood, MN). The final concentration of each inoculum was about 10-300 colony forming unit (cfu) counts per 100 mL.

As a reference, a 1 mL sample of inoculum was taken immediately prior to the final dilution step. The sample was plated onto a PETRIFILM *E coli*./Coliform Count Plate (3 M Corporation, Maplewood, MN), incubated, and counted according to the manufacturer's instructions.

TABLE 1

Bacterial Strains used in Examples

Eschericha coli (ATCC 25922)
Eschericha coli (ATCC 11229)
Eschericha coli (ATCC 23M-FR8)
Eschericha coli (ATCC 8739)
Eschericha coli (ATCC 51813)
Enterobacter amnigenus (ATCC 51816)
Enterobacter amnigenus (ATCC 51818)
Salmonella enterica (ATCC 51812)
Salmonella typhimurian (ATCC 51812)
Enterococcus faecalis (ATCC 14506)
Enterococcus faecalis (ATCC 29212)
Enterococcus faecalis (ATCC 19433)
Hafnia alvei (ATCC 51815)
Kiebsiela oxytoc (ATCC 51817)
Pseudomonas aeruginosa (ATCC 27853)

Nutrient Formulations

Nutrient Formulation A was prepared by dissolving 35.6 g of Acumedia Lauryl Sulfate Broth (obtained from Neogen Corporation, Lansing, MI) in 1 L of purified water and supplementing with 0.6 g of BCIG.

Nutrient Formulation B was prepared by dissolving 71.2 g of Acumedia Lauryl Sulfate Broth in 1 L of purified water and supplementing with 0.6 g of BCIG.

Nutrient Formulation C was prepared by dissolving 71.2 g of Acumedia Lauryl Sulfate Broth in 1 L of purified water and supplementing with 0.8 g of sodium lauryl sulfate and 0.6 g of BCIG.

Nutrient Formulation D was prepared by dissolving 71.2 g of Acumedia Lauryl Sulfate Broth in 1 L of purified water and supplementing with 1.8 g of sodium lauryl sulfate and 0.6 g of BCIG.

Nutrient Formulation E was prepared by dissolving 71.2 g of Acumedia Lauryl Sulfate Broth in 1 L of purified water and supplementing with 3.8 g of sodium lauryl sulfate and 0.6 g of BCIG.

Nutrient Formulation F was prepared by dissolving 71.2 g of Acumedia Lauryl Sulfate Broth in 1 L of purified water and supplementing with 3.8 g of sodium lauryl sulfate, 0.31 g of O-methyl-beta-D-glucuronide, 0.8 g of IPTG, 0.6 g of 6-chloro-3-indoxyl-beta-D-galactopyranoside, and 0.6 g of BCIG.

TABLE 2

Composition of Nutrient Formulations A-F

| Ingredient | Concentration of Components in Nutrient Formulations (g/L) | | | | | |
|---|---|---|---|---|---|---|
|  | A | B | C | D | E | F |
| Enzymatic Digest of Casein | 20 | 40 | 40 | 40 | 40 | 40 |
| Lactose | 5 | 10 | 10 | 10 | 10 | 10 |
| Sodium chloride | 5 | 10 | 10 | 10 | 10 | 10 |
| Monopotassium phosphate | 2.75 | 5 | 5 | 5 | 5 | 5 |
| Disodium phosphate | 2.75 | 5 | 5 | 5 | 5 | 5 |
| Sodium lauryl sulfate | 0.1 | 0.2 | 1.0 | 2.0 | 4.0 | 4.0 |
| BCIG | 0.6 | 0.6 | 0.6 | 0.6 | 0.6 | 0.6 |
| O-methyl-beta-D-glucuronide | 0 | 0 | 0 | 0 | 0 | 0.31 |
| IPTG | 0 | 0 | 0 | 0 | 0 | 0.8 |
| 6-chloro-3-indoxyl-beta-D-galactopyranoside | 0 | 0 | 0 | 0 | 0 | 0.6 |

Example 1

Microbial detection devices were prepared according to FIG. 7. The second wall portion consisted of a 127 mm by 152.4 mm piece of clear BOPP film (1.6 mil (0.04 mm) thick and corona treated on both sides). The absorbent pad was a 101.6 mm by 127 mm piece of Gelok 30040-0305 superabsorbent polymer (SAP) laminate (300 g/m$^2$ of sodium polyacrylate granules laminated between tissue layers, Gelok Industries, Dunbridge, OH). The membrane filter was a 101.6 mm by 127 mm piece of DURAPES 450 Membrane (5.5 mil (0.14 mm) thick hydrophilic polyethersulfone membrane for microfiltration obtained from the 3 M Corporation, Maplewood, MN). A 101.6 mm by 127 mm piece of Fitesa-ADL2 non-woven material (Fitesa Company, Simpsonville, SC) was adhesively laminated between the SAP laminate and membrane using hot melt adhesive (#H4073 A, Bostik Company, Milwaukee, WI). The resulting laminate was placed and centered on the inner surface of the second wall portion oriented such that the absorbent pad faced the inner surface of the second wall. In the orientation of this construction, a 12.7 mm strip along the perimeter of the inner surface of the second wall portion was not covered.

A frame layer was prepared by first coating one side of a clear BOPP film (1.6 mil (0.04 mm) thick and corona treated on both sides) with an isooctyl acrylate/acrylamide (98/2 weight ratio) pressure sensitive adhesive according to the method described in Example 4 of U.S. Pat. No. 5,409,838. The coated film was subsequently cut to form a frame having external dimensions of 127 mm by 152.4 mm and a centered 76.2 mm by 101.6 mm internal opening. The resulting frame had a 25.4 mm wide adhesively coated border. The frame then was adhesively attached to the membrane filter and the inner surface of the second wall creating a partially constructed device that had a 76.2 mm by 101.6 mm section of the membrane uncovered on one side.

A separate sheet of clear BOPP film (1.6 mil thick and corona treated on both sides) was knife-coated with Nutrient Formulation C at 14 mil gap setting (Table 2). The nutrient coated substrate was dried in an oven at 85° C. for 12 minutes. An isooctyl acrylate/acrylic acid (98/2 weight ratio) pressure-sensitive adhesive coating formulation containing TTC as described in Example 4 of U.S. Pat. No. 5,409,838 was knife-coated onto the exposed nutrient coating with a 2 mil (0.05 mm) gap setting. The resulting coated film was dried in an oven at 65° C. for 6 minutes. The adhesive coated side of the film was then powder coated with guar gum (Danisco Company, Denmark). The powder was evenly applied and excess powder was removed from the adhesive layer by hand shaking of the film followed by lightly brushing the surface with a paper towel. The film sheet was cut into a 76.2 mm wide by 101.6 mm long section and then placed to cover the previously uncovered membrane of the partially constructed device. The film was oriented such that the coated side of the film faced the membrane. The sodium lauryl sulfate content of the coated film was 2.35 mg per 12 in$^2$ of film surface.

The first wall portion consisted of a 127 mm by 152.4 mm piece clear BOPP film (1.6 mil (0.04 mm) thick and corona treated on both sides) that had been coated on one side with an isooctyl acrylate/acrylamide (98/2 weight ratio) pressure sensitive adhesive according to the method described in Example 4 of U.S. Pat. No. 5,409,838. A one inch wide piece of silicone coated paper release liner was attached along one of the 127 mm edges on the coated surface of the first wall portion. The first wall portion was then edge aligned with and adhesively laminated to both the uncoated surface of the nutrient coated BOPP film and the surface of the frame layer that faced away from the second wall portion. This construction resulted in a pouch with an opening to a first compartment defined in part by the first wall portion and the membrane filter.

Separate detection devices were inoculated with an inoculum of a single microbial sample selected from Table 1. The final dilution of the inoculum sample (100 mL, procedure described above) was poured into the first compartment of a pouch device. The release liner on the pouch was removed and the first compartment was sealed. The device was then placed on a flat, horizontal surface (outer surface of the second wall portion facing the horizontal surface) in an incubator and maintained at 37° C. for 48 hours. The red and blue-colored colonies (cfu) in each device were counted by visual examination at the end of the incubation period. The results are presented in Table 3. The notation "positive" in Tables 3 and 4 indicates that colonies (cfu) were observed. The notation "negative" in Tables 3 and 4 indicates that colonies (cfu) were not observed.

Example 2

Microbial detection devices were prepared as described in Example 1 with the exception that the BOPP film was coated with Nutrient Formulation D (Table 2), instead of Nutrient Formulation C. The resulting sodium lauryl sulfate content of the coated film was 4.46 mg per 12 in$^2$ of film surface. The devices were inoculated and visually examined for colonies according to the procedure described in Example 1. The results are presented in Table 3.

Example 3

Microbial detection devices were prepared as described in Example 1 with the exception that the BOPP film was coated with Nutrient Formulation E (Table 2), instead of Nutrient Formulation C. The resulting sodium lauryl sulfate content of the coated film was 7.43 mg per 12 in$^2$ of film surface. The devices were inoculated and visually examined for colonies according to the procedure described in Example 1. The results are presented in Tables 3 and 4.

Example 4

Microbial detection devices were prepared as described in Example 1 with the exception that the BOPP film was coated with Nutrient Formulation F (Table 2), instead of Nutrient Formulation C. The resulting sodium lauryl sulfate content of the coated film was 9.52 mg per 12 in$^2$ of film surface. The devices were inoculated and visually examined for colonies according to the procedure described in Example 1. The results are presented in Table 5.

Comparative Example 1

Microbial detection devices were prepared as described in Example 1 with the exception that the BOPP film was coated with Nutrient Formulation A (Table 2), instead of Nutrient Formulation C. The resulting sodium lauryl sulfate content of the coated film was 0.46 mg per 12 in$^2$ of film surface. The devices were inoculated and visually examined for colonies according to the procedure described in Example 1. The results are presented in Table 3.

Comparative Example 2

Microbial detection devices were prepared as described in Example 1 with the exception that the BOPP film was coated with Nutrient Formulation B (Table 2), instead of Nutrient Formulation C. The resulting sodium lauryl sulfate content of the coated film was 0.74 mg per 12 in$^2$ of film surface. The devices were inoculated and visually examined for colonies according to the procedure described in Example 1. The results are presented in Table 3.

TABLE 3

Colonies (cfu) observed using Devices and Methods of Examples 1-3 and Comparative Examples 1-2.

| | Colonies (cfu) Observed | | | | |
|---|---|---|---|---|---|
| | Example 1 | Example 2 | Example 3 | Comparative Example 1 | Comparative Example 2 |
| Eschericha coli (ATCC 25922) | positive | positive | positive | positive | positive |
| Enterococcus faecalis (ATCC 29212) | positive | positive | negative | positive | positive |

TABLE 4

Colonies (cfu) observed using Device and Method of Example 3

| | Colonies (cfu) observed with Example 3 |
|---|---|
| Eschericha coli (ATCC 25922) | positive |
| Eschericha coli (ATCC 11229) | positive |
| Eschericha coli (ATCC 23M-FR8) | positive |
| Eschericha coli (ATCC 8739) | positive |
| Enterobacter amnigenus (ATCC 51816) | positive |
| Enterobacter amnigenus (ATCC 51818) | positive |
| Salmonella enterica (ATCC 51812) | positive |
| Enterococcus faecalis (ATCC 14506) | negative |
| Enterococcus faecalis (ATCC 29212) | negative |
| Enterococcus faecalis (ATCC 19433) | negative |
| Hafnia alvei (ATCC 51815) | positive |
| Kiebsiela oxytoc (ATCC 51817) | positive |
| Pseudomonas aeruginosa (ATCC 27853) | positive |

TABLE 5

Colonies (cfu) observed using Device and Method of Example 4

| | Colonies (cfu) observed with Example 4 |
|---|---|
| Enterobacter amnigenus (ATCC 51816) | positive (salmon colored) |
| Eschericha coli (ATCC 51813) | positive (dark blue colored) |
| Salmonella typhimurian (ATCC 51812) | negative |
| Enterococcus faecalis (ATCC 14506) | negative |
| Enterococcus faecalis (ATCC 29212) | negative |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:

1. A microbial detection device, comprising:
a water-proof pouch comprising:
a first wall portion having an inner surface and an outer surface;
a second wall portion having an inner surface and an outer surface;
a porous membrane filter disposed in the pouch between the inner surface of the first wall portion and the inner surface of the second wall portion, the membrane filter having a first major surface and a second major surface opposite the first major surface;
a first compartment defined in part by inner surface of the first wall portion and defined in part by the first major surface of the membrane filter;
a sealable sample port that provides access to deposit a liquid into the first compartment;
an effective amount of a dry nutrient disposed in the first compartment, the dry nutrient comprising sodium lauryl sulfate in an amount of 4 milligrams (mg) or greater per 12 square inches ($in^2$) of the inner surface of the first wall portion;
a second compartment defined in part by the inner surface of the second wall portion and defined in part by the second major surface of the membrane filter;
wherein the membrane filter permits passage of aqueous liquids from the first compartment to the second compartment and prevents passage of particles of a predetermined size from the first compartment to the second compartment;
a dry cold water-soluble gelling agent adhered to the pouch in the first compartment; and
an absorbent pad disposed in the second compartment.

2. The microbial detection device of claim 1, further comprising an indicator reagent for indicating a presence of a viable microorganism, wherein the indicator reagent is disposed in the pouch.

3. The microbial detection device of claim 1, comprising at least one of a lactose-fermentation indicator system, a redox indicator system, or a beta-D-glucuronidase indicator system.

4. The microbial detection device of claim 3, wherein the lactose-fermentation indicator system comprises lactose, a pH indicator, an inducer compound, and 2,3,5-triphenyl tetrazolium chloride (TTC).

5. The microbial detection device of claim 3, wherein the beta-D-glucuronidase indicator system comprises 5-bromo-4-chloro-3-indolyl-beta-D-glucuronide, and at least one of methyl-beta-D-glucuronide, phenyl-beta-D-glucuronide, and D-glucuronic acid.

6. The microbial detection device of claim 2, wherein the indicator reagent is a first indicator reagent and wherein the microbial detection device further comprises a second indicator reagent.

7. The microbial detection device of claim 6, wherein the first indicator reagent is a beta-D-glucuronidase substrate and the second indicator reagent is a beta-D-galactosidase substrate.

8. The microbial detection device of claim 6, wherein the first indicator reagent is 2,3,5-triphenyl tetrazolium chloride, a pH indicator, or a beta-D-galactosidase substrate, and the second indicator reagent is a glucuronidase substrate selected from the group consisting of p-nitrophenyl-beta-glucuronide, p-nitrophenyl-2,3,4-tri-O-acetyl-beta-glucuronic acid methyl ester, phenolphthalein glucuronic acid, phenolphthalein mono-P-glucuronic acid, naphthyl-AS-BI-beta-D-glucuronide, 4-methylumbelliferyl-beta-D-glucuronide, sodium salt of 8-Hydroxyquinoline-beta-D-glucuronic acid, sodium salt of 2-Naphthyl-beta-D-glucuronic acid, sodium salt of 4-Nitrophenyl-beta-D-glucuronic acid, sodium salt monohydrate of Phenolphthalein-beta-D-glucuronic acid, cyclohexylammonium salt of 5-Bromo-4-chloro-3-indoxyl-beta-D-glucuronic acid, cyclohexylammonium salt of 3-Indoxyl-beta-D-glucuronic acid, sodium salt of 3-Indoxyl-beta-D-glucuronic acid, cyclohexylammonium salt of 5-Bromo-6-chloro-3-indoxyl-beta-D-glucuronic acid, anhydrous sodium salt of 5-Bromo-4-chloro-3-indoxyl-beta-D-glucuronic acid, and sodium salt trihydrate of 5-Bromo-4-chloro-3-indoxyl-beta-D-glucuronic acid.

9. The microbial detection device of claim 8, further comprising an inducer disposed in the first compartment, wherein the inducer is selected from the group consisting of isopropyl-beta-D-thiogalactoside (IPTG), phenyl-beta-D-galactoside, methyl-beta-D-glucuronide, D-glucuronic acid, and combinations thereof.

10. The microbial detection device of claim 1, wherein the dry nutrient comprises 4.5 mg or greater sodium lauryl sulfate per 12 $in^2$ of a surface of the first compartment.

11. The microbial detection device of claim 1, wherein the membrane filter comprises polyether sulfone.

12. The microbial detection device of claim 1, wherein the dry nutrient is present in a coat weight of 50 to 550 mg per 24 $in^2$ adhered to the first wall or to the second wall of the first compartment.

13. A method comprising:
placing a predetermined volume of aqueous sample into the first compartment of the microbial detection device of claim 1;
sealing the sample port;

incubating the device for a period of time at a temperature that facilitates growth and detection of a target microorganism; and detecting a presence or an absence of a colony of the target microorganism in the device.

14. The method of claim 13, wherein the aqueous sample contains Gram negative bacteria.

15. The method of claim 14, wherein the aqueous sample further contains Gram positive bacteria; and wherein the method further comprises counting Gram negative bacteria colonies separately from Gram positive bacteria colonies.

16. The method of claim 14, wherein the aqueous sample contains at least one coliform; and wherein the detecting comprises enumerating a colony of the at least one coliforms.

17. The method of claim 14, wherein the aqueous sample contains at least one strain of *Escherichia coli*; and wherein the detecting comprises enumerating a colony of the at least one strain of *Escherichia coli*.

\* \* \* \* \*